United States Patent
Noda et al.

(10) Patent No.: US 7,358,098 B2
(45) Date of Patent: Apr. 15, 2008

(54) DEVICE FOR CAPTURING BEADS AND METHOD AND APPARATUS FOR ARRAYING BEADS

(75) Inventors: Hideyuki Noda, Kokubunji (JP); Yoshinobu Kohara, Mitaka (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 238 days.

(21) Appl. No.: 11/195,701

(22) Filed: Aug. 3, 2005

(65) Prior Publication Data
US 2006/0257994 A1  Nov. 16, 2006

(30) Foreign Application Priority Data
May 13, 2005  (JP) ............................. 2005-141569

(51) Int. Cl.
*G01N 33/543* (2006.01)
(52) U.S. Cl. ..................................................... 436/518
(58) Field of Classification Search ............... 436/518; 435/283.1, 286.7–287.3, 288.4; 422/58, 422/62–66
See application file for complete search history.

(56) References Cited

U.S. PATENT DOCUMENTS

| | | | |
|---|---|---|---|
| 3,941,565 A * | 3/1976 | Schwartz | ................. 205/781.5 |
| 5,935,859 A | 8/1999 | Elliott et al. | |
| 6,023,540 A | 2/2000 | Walt et al. | |
| 6,255,116 B1 | 7/2001 | Leber et al. | |
| 2003/0198575 A1 | 10/2003 | Noda et al. | |
| 2004/0265181 A1 | 12/2004 | Noda et al. | |

FOREIGN PATENT DOCUMENTS

| | | |
|---|---|---|
| EP | 1 522 340 A1 | 9/2004 |
| JP | 11-243997 | 3/1998 |
| JP | 2000-346842 | 4/2000 |
| JP | 2003-315336 | 4/2002 |
| JP | 2005-017224 | 6/2003 |

OTHER PUBLICATIONS

H. Noda et al., "Automated Bead Alignment Apparatus Using a Single Bead Capturing Technique for Fabrication of a Miniaturized Bead-Based DNA Probe Array", Anal. Chem., vol. 75, No. 13 (Jul. 1, 2003), pp. 3250-3255.
S. Fodor et al., "Light-Directed,Spatially Addressable Parallel Chemical Synthesis", Science, vol. 251 (Feb. 15, 1991), pp. 767-773.
M. Schena et al., "Quantitative Monitoring of Gene Expression Patterns with a Complementary DNA Microarray", Science, vol. 270 (Oct. 20, 1995), pp. 467-470.
T. Okamoto et al., "Microarray Fabrication with Covalent Attachment of DNA Using Bubble Jet Technology", Nature Biotechnology, vol. 18 (Apr. 2000), pp. 438-441.
R. J. Fulton et al., "Advanced Multiplexed Analysis with the FlowMetrix™ System", Clinical Chemistry, vol. 43, No. 9 (1997), pp. 1749-1756.
Y. Kohara et al., "DNA Probes on Beads Arrayed in a Capillary, 'Bead-array', Exhibited High Hybridization Performance", Nucleic Acids Research (2002), vol. 30, No. 16, pp. 1-7.

\* cited by examiner

*Primary Examiner*—Ann Y. Lam
(74) *Attorney, Agent, or Firm*—Reed Smith LLP; Stanley P. Fisher, Esq.; Juan Carlos A. Marquez, Esq.

(57) ABSTRACT

Beads having diameters of several tens of micrometers to several millimeters and immobilized with biomolecules are captured by one kind of bead capturing nozzle one by one without fail. Using a bead holding plate having a plurality of wells each of which holds a plurality of the beads and a solution, a vibration generator mounted with a stage to attach the bead holding plate, and a bead capturing nozzle for bead capture connected to a suction pump, only a single bead is captured at the tip of the bead capturing nozzle by inserting the nozzle having an inner diameter smaller than the beads and a negative pressure inside created by the pump into the solution to allow the nozzle to come in contact with the beads in the well, applying a vibration to the bead holding plate by the vibration generator, and withdrawing the bead capturing nozzle into the air.

18 Claims, 19 Drawing Sheets

FIG. 3 A
FIG. 3 B
FIG. 3 C
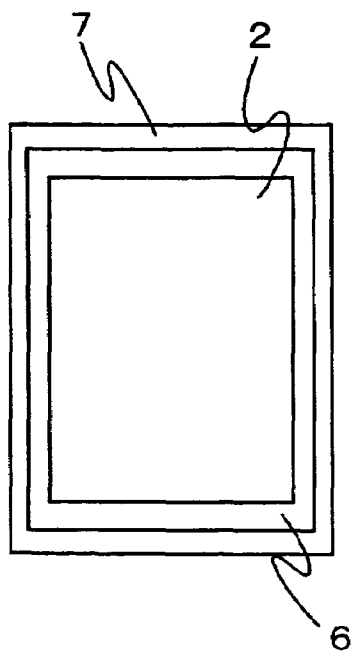
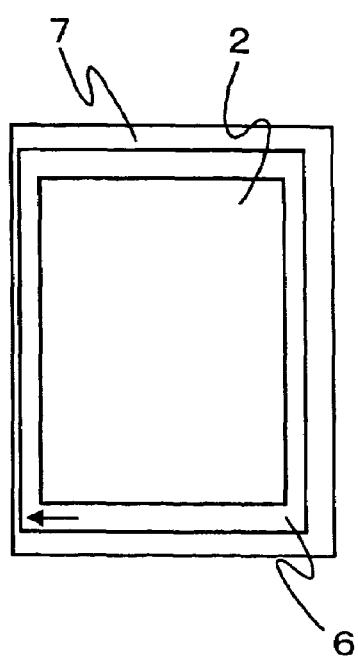
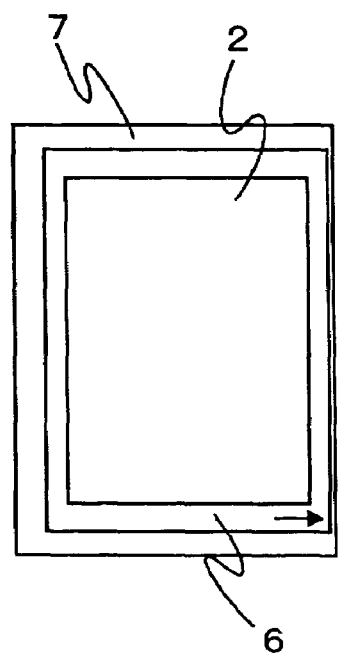
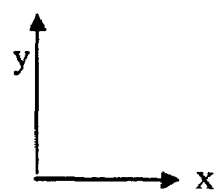

FIG. 12 A
FIG. 12 B
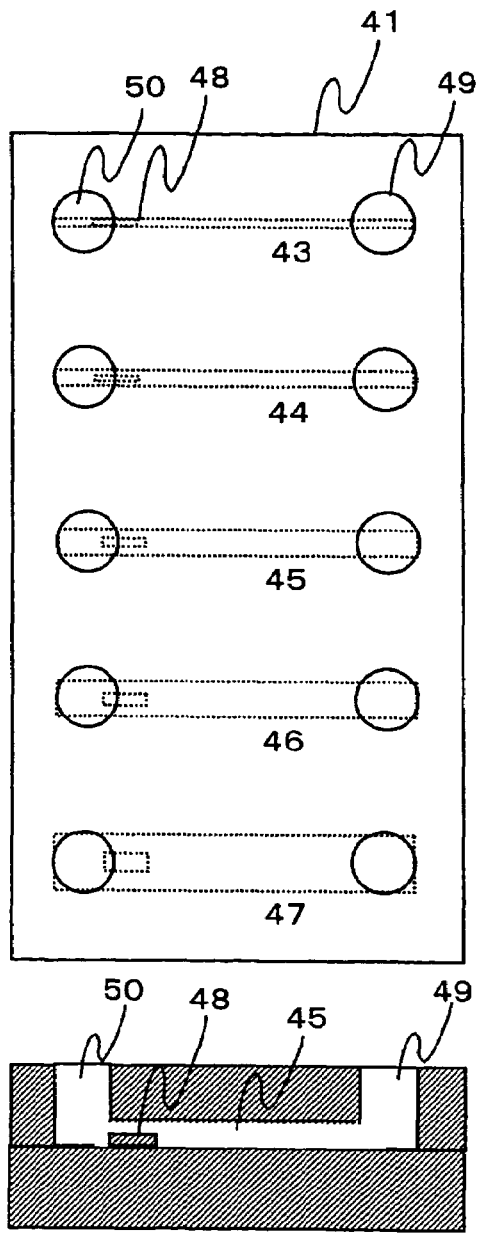
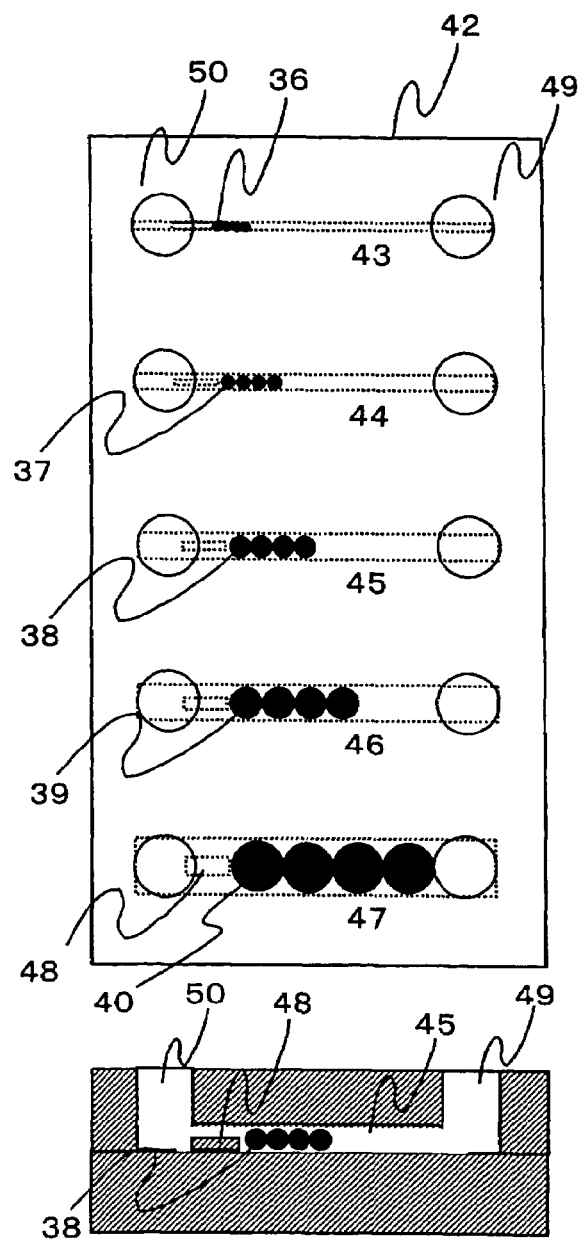

FIG. 14 A
FIG. 14 B
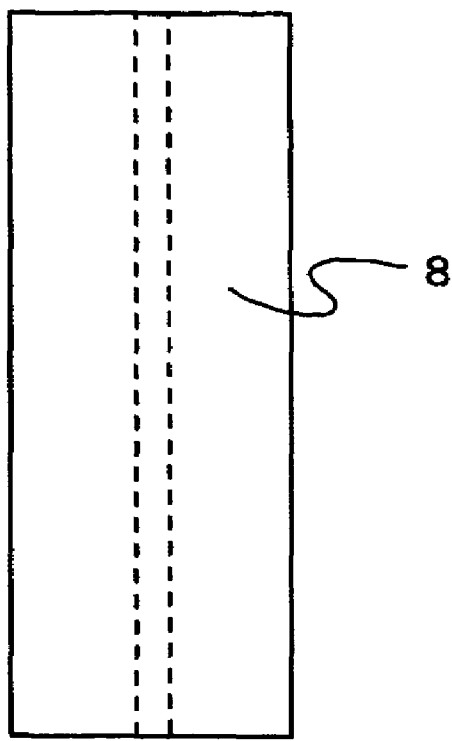
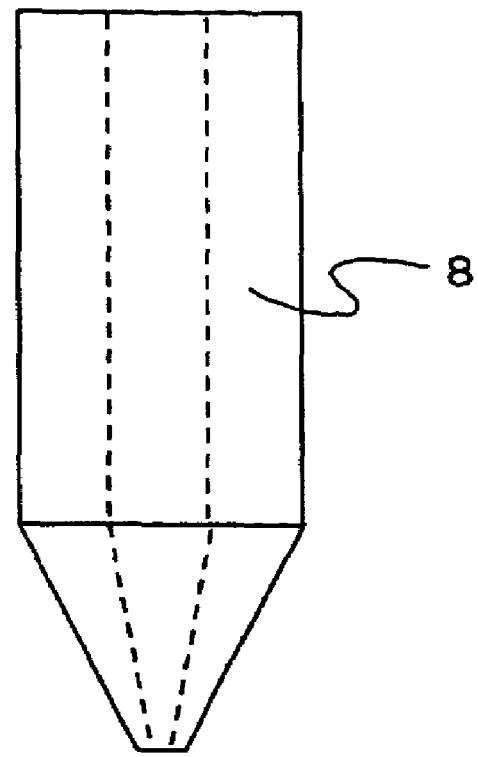

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<221> NAME/KEY: location of a fluorophore-tag
<222> LOCATION: 1; (8)...(11)
<223> OTHER INFORMATION: DNA primer incorporating a fluorophore-tag and
      n is a, c, g or t

<400> SEQUENCE: 1
atctgactnn ngctcctc                                                 18

<210> SEQ ID NO 2
<211> LENGTH: 18
<212> TYPE: DNA
<213> ORGANISM: Artificial Sequence
<220> FEATURE:
<221> NAME/KEY: location of a fluorophore-tag
<222> LOCATION: 1; (8)...(11)
<223> OTHER INFORMATION: DNA primer incorporating a fluorophore-tag and
      n is a, c, g or t

<400> SEQUENCE: 2
ctacctgcnn nctggacg                                                 18

<210> SEQ ID NO 3
<211> LENGTH: 18
<212> TYPE: DNA
<213> ORGANISM: Artificial Sequence
<220> FEATURE:
<221> NAME/KEY: location of a fluorophore-tag
<222> LOCATION: 1; (8)...(11)
<223> OTHER INFORMATION: DNA primer incorporating a fluorophore-tag and
      n is a, c, g or t

<400> SEQUENCE: 3
gaggagccnn ngtcagat                                                 18

<210> SEQ ID NO 4
<211> LENGTH: 18
<212> TYPE: DNA
<213> ORGANISM: Artificial Sequence
<220> FEATURE:
<221> NAME/KEY: location of a fluorophore-tag
<222> LOCATION: 1; (8)...(11)
<223> OTHER INFORMATION: DNA primer incorporating a fluorophore-tag and
      n is a, c, g or t

<400> SEQUENCE: 4
cgtccaggnn ncaggtag                                                 18

DEVICE FOR CAPTURING BEADS AND METHOD AND APPARATUS FOR ARRAYING BEADS

CLAIM OF PRIORITY

The present application claims priority from Japanese application JP 2005-141569 filed on May 13, 2005, the content of which is hereby incorporated by reference into this application.

FIELD OF THE INVENTION

The present invention relates to a device for capturing beads to manipulate beads with biomolecular probes such as DNA, RNA, and protein immobilized on their surface one by one and to a method and apparatus for arraying beads to arrange the beads in a container by manipulating a plurality of beads one by one.

BACKGROUND OF THE INVENTION

With the progress of the genome project, activities to understand the cause of a disease and life phenomenon through understanding an organism at its DNA level have become very active. For understanding the life phenomenon and gene function, studies on gene expression are effective. As a promising method to study this gene expression, probe array, so-called DNA chip, in which a number of DNA probes are immobilized on a solid surface such as slide glass by sorting them out for every kind has come into use. The method of producing DNA chips includes a method in which a nucleotide oligomer with a designed sequence is synthesized base by base in a large number of sectioned cells using a lithography technology widely used in a photochemical reaction and a semiconductor industry (Science 251, 767-773 (1991)) and a method in which a plurality of kinds of DNA probes are spotted one by one to each section (Science 270, 467-470 (1995); Nat. Biotechnol. 18, 438-441 (2000)).

When a DNA chip is produced, the DNA probes need to be immobilized on an array piece by piece or the oligomers need to be synthesized base by base in any of these methods, and its production requires both time and manpower, leading to a high cost. In addition, since the probes are immobilized by applying liquid droplets containing them on a solid surface, there are problems that spot-to-spot variation may result, changing a combination of kinds of the probes is not easy, handling by a user is difficult, and so forth.

In order to solve the above problems, a probe array, that is, bead array in which beads immobilized with DNA probes are prepared and a plurality of kinds of these beads are lined up has been disclosed (Clinical Chemistry 43, 1749-1756 (1997); Nucleic Acids Research 30, e87 (2002); Specification of U.S. Pat. No. 6,023,540). The advantage of the probe array with beads lies in that a probe array without variations in the probe density for each bead can be produced because a method of probe immobilization with the use of a chemical reaction in a solution can be employed.

In the DNA chip, the identification of a probe is performed by way of the location of oligomer synthesis or the spot of each DNA probe. In the probe array having beads immobilized with probes, the identification of a probe is performed by way of beads colored differently for each probe (Clinical Chemistry 43, 1749-1756 (1997); Specification of U.S. Pat. No. 6,023,540) or the order of beads arrayed in a capillary (Nucleic Acids Research 30, e87 (2002)).

For the identification and quantitative analysis of a plurality of kinds of DNA contained in an analyte sample with a DNA chip, the sample is allowed to react with oligomers or DNAs immobilized on the chip over half a day to a day. On the other hand, in a probe array arranged with beads in a capillary, that is, bead array, an analyte sample is forced to flow through the capillary. Since the time required for gene examination with the bead array can be shortened compared with a conventional method, the bead array is a technique of measurement suitable for application at a clinical site such as hospital. For example, the use of bead array can be expected as a means for prompt detection of an infectious disease requiring an urgent diagnosis and a foreign gene non-existent in human and derived from the genome of a pathogenic microorganism in bacteriological examination and the like.

For practical use of a bead array employing a method in which probes are identified from the order of beads arranged in a capillary (Nucleic Acids Research 30, e87 (2002)), it is essential to establish a method for selecting arbitrary beads immobilized with probes according to specific examination purpose and arraying the beads as one desires, and several methods have been proposed for this. For example, there are a method in which beads are poured into a capillary by making use of a liquid flow while controlling individual beads one by one (JP-A No. 243997/1999) and another method in which only one bead is retained on a sheet provided with a fine recess in which only one bead from among a plurality of the beads introduced with a solvent can be put and the sheet is moved to a position of a capillary or a slot provided on a flat plate while retaining the bead, followed by arraying the bead one after another (JP-A No. 346842/2000). However, these methods often fail to incorporate beads because of the influence of air bubbles, and therefore there was a problem in reliability and usability.

Hence, a method in which only one bead is captured at the suction tip of a bead capturing nozzle from among a plurality of the beads immobilized with the same probe with the use of the bead capturing nozzle (JP No. 3593525; JP-A No. 17224/2005; Analytical Chemistry 75, 3250-3255(2003)). According to this method, beads can be arrayed in the order as intended. In order to capture only one bead at the suction tip of the bead capturing nozzle, beads additionally attached to the side surface of the bead capturing nozzle due to static electricity need to be removed. For this purpose, the surface tension of the air-liquid interface that arises at the border of the air and a solution is utilized as a means. The extra beads attached to the sidewall of the bead capturing nozzle cannot be passed through the interface and are retained on the solution side of the interface when the bead capturing nozzle is withdrawn from the solution into the air. Since the beads retained on the interface cannot be dislocated into the air, the beads attached to the sidewall of the bead capturing nozzle slide down along the sidewall and left behind in the solution. As the result, only one bead held via suction is captured by the bead capturing nozzle after withdrawing the bead capturing nozzle into the air. It should be noted that extra beads attached to the tip surface are taken out into the air since the tip surface of the nozzle is not influenced by the force from the air-liquid interface. To prevent this from occurring, it is necessary not to provide any space at the tip surface that allows bead attachment besides the suction portion, and therefore it has been necessary to use the bead capturing nozzle having an outer diameter approximately equal to that of the bead.

SUMMARY OF THE INVENTION

Glass beads and plastic beads used for immobilization of biomaterials had large variations in size, and even when a bead capturing nozzle prepared by adjusting beforehand to the size of the beads was used, two or more beads were often captured at the tip surface of the bead capturing nozzle. On the other hand, when beads having different diameters were arrayed on the same array by a method in which a conventional bead capturing nozzle was used, bead capturing nozzles suitable for each size of the beads to be captured had to be prepared because the outer diameter of the bead capturing nozzle was limited by the bead diameter.

The objects of the present invention are to provide a device for capturing beads one by one that can reliably capture and manipulate beads individually without depending too much on bead outer diameter and an apparatus for arraying beads with the use of the device for capturing beads one by one.

In the present invention, a bead holding plate having a plurality of chambers each of which can hold a plurality of beads and a solution, a vibration generator mounted with a stage where the bead holding plate is arranged, and a bead capturing nozzle that is connected to a suction pump and operated by aspirating its tip to capture the bead are used.

The device for capturing beads one by one of the present invention is provided with at least a chamber to hold the solution containing the plurality of beads, the vibration generator to vibrate the chamber, the long and narrow bead capturing nozzle to capture the bead at its tip, the suction pump connected to the bead capturing nozzle, and an actuator to insert the tip of the bead capturing nozzle into the solution in the chamber as well as to lift it up. An opening formed at the tip of the bead capturing nozzle is smaller than the diameter of the beads and the outer diameter of the tip of the bead capturing nozzle is larger than the diameter of the beads. The vibration generator generates a vibration of a frequency equal to or higher than 20 Hz. The amplitude of the vibration is preferably equal to or larger than 0.1 mm.

The method for arraying beads according to the present invention includes the steps of inserting the bead capturing nozzle, which has the opening smaller than the diameter of the beads formed at the tip and the outer diameter of the tip larger than the diameter of the beads, into the solution containing a plurality of beads immobilized with a biomolecular probe on the surface, exerting a suction force on the tip of the bead capturing nozzle, vibrating the chamber, withdrawing the bead capturing nozzle retaining one bead at the tip via suction from the solution in the chamber, and introducing the bead retained at the tip of the bead capturing nozzle via suction into a bead array container.

The apparatus for arraying beads is provided with the stage to retain a plurality of chambers to hold solutions each containing a plurality of beads, the bead capturing nozzle having the opening smaller than the diameter of the beads formed at the tip and the outer diameter of the tip larger than the diameter of the beads, the actuator to drive the bead capturing nozzle, a vacuum/pressure unit to develop a negative or positive pressure at the tip of the bead capturing nozzle, a vibration unit to vibrate the stage, a holder for bead array container that retains a bead array container to hold beads, and a control unit, where the control unit allows the bead capturing nozzle to be inserted into the vibrating chamber on the stage by controlling the actuator, the bead capturing nozzle to be lifted up from the chamber by controlling the actuator in a state that a single bead is captured at the tip of the bead capturing nozzle by controlling the vacuum/pressure unit to develop a negative pressure at the tip of the bead capturing nozzle, the bead capturing nozzle capturing a single bead at the tip to be moved to the position of the bead array container by controlling the actuator, and the captured bead to be introduced into the bead array container by controlling the vacuum/pressure unit to develop a positive pressure at the tip.

According to the present invention, a single bead can be captured from among the beads immobilized with biomolecules without fail, and a bead array arranged with captured beads can be efficiently produced at low cost.

BRIEF DESCRIPTION OF THE DRAWINGS

FIGS. 3A to 3C are diagrams explaining a rocking vibration of the bead holding plate;

FIG. 7A is a microphotographic diagram showing a state that the bead capturing nozzle is inserted into the beads, FIG. 7B is a microphotographic diagram showing the moment when the bead capturing nozzle is separated from the beads, and FIG. 7C is a microphotographic diagram showing a state that the tip of the bead capturing nozzle is withdrawn into the air;

FIG. 8A is a microphotographic diagram showing a state that the bead capturing nozzle is inserted into the beads, FIG. 8B is a microphotographic diagram showing the moment when the bead capturing nozzle is separated from the beads, and FIG. 8C is a microphotographic diagram showing a state that the tip of the bead capturing nozzle is withdrawn into the air;

FIG. 11A is a diagram explaining its method and FIG. 11B is a diagram explaining its result;

FIGS. 12A and 12B represent schematic diagrams showing a bead array chip for arranging beads having different diameters in a plurality of flow channels respectively, where FIG. 12A is a schematic diagram of the chip before arraying the beads and FIG. 12B is a schematic diagram of the chip after arraying the beads;

FIGS. 14A and 14B represent schematic diagrams of the bead capturing nozzle.

DETAILED DESCRIPTION OF THE PREFERRED EMBODIMENTS

Hereinafter, embodiments of the present invention are explained with reference to the accompanying drawings.

Figure 1:
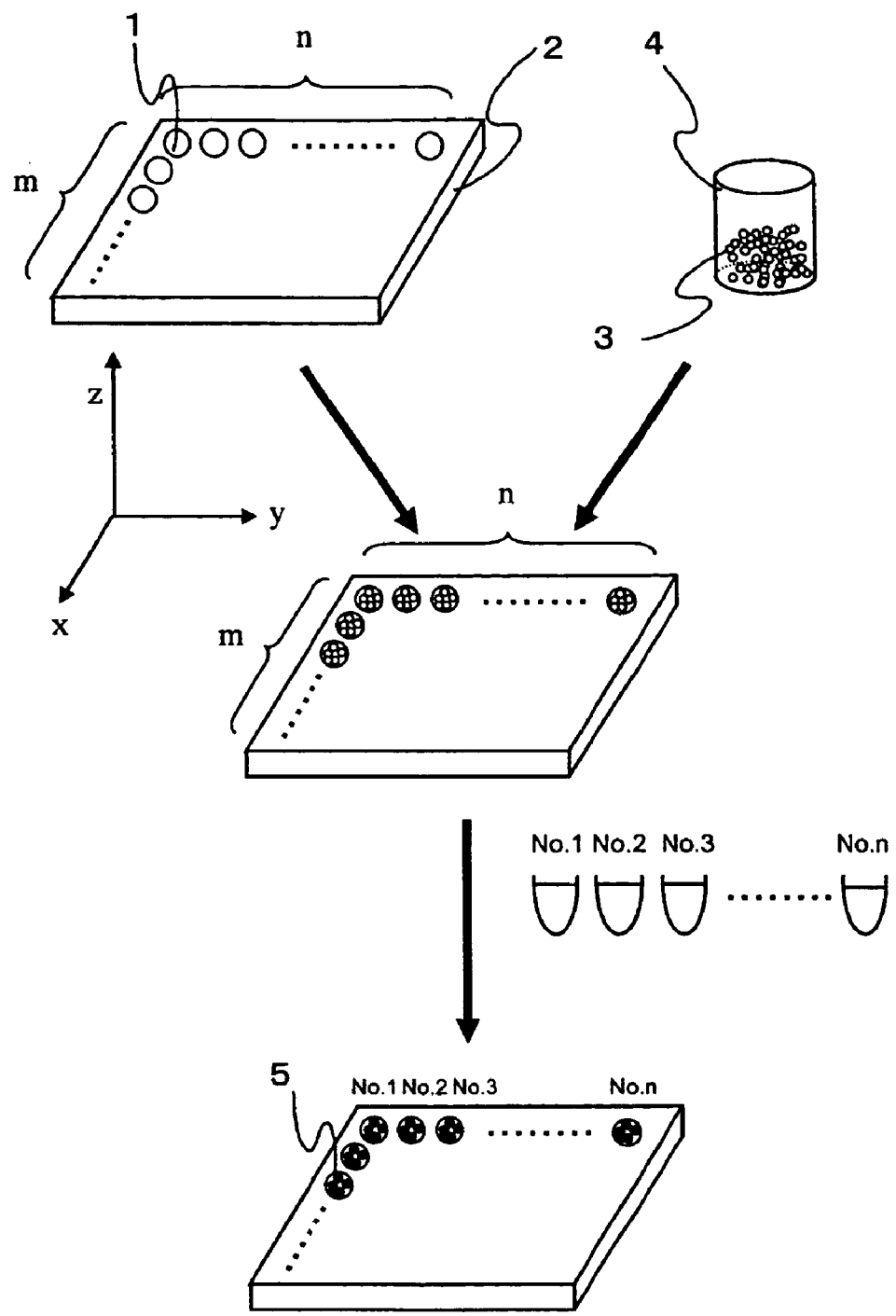
FIG. 1 is a diagram explaining a method for preparing beads and a structure example of a bead holding plate.

First, the method for preparing beads immobilized with biomolecules on their surface is explained with the use of FIG. 1. A bead holding plate 2 having the m×n number of wells 1, groups of beads, and a plurality of kinds of biomolecular probes such as DNA, RNA, and protein that modify beads 3 are prepared. The wells 1 on the prepared bead holding plate 2 are spaced uniformly not only in the x direction at intervals of a first center distance but also in the y direction perpendicular to the x direction at intervals of a second center distance. The well 1 has a circular upper opening and a central axis parallel to the z direction, and is either in a cylindrical or cone shape having a bottom portion. As the bead holding plate 2 having such a plurality of the wells 1, for example, a commercially available 384-well microtiter plate can be used. Preferably the beads 3 to be used are 10 micrometers or larger in diameter and in a spherical shape when a commercially available capillary is used for capturing beads, while beads of several micrometers in diameter can also be used when a nozzle exclusively for capturing beads that is micro-fabricated by semiconductor etching technology is used.

The beads 3 prepared in a several mg unit are distributed to each well on the bead holding plate 2 from a bead container 4 using a spatula. Then, different kinds of probes are introduced onto the beads present in a row of the wells 1 as a unit or in each well 1, and the probes are immobilized on the surfaces of all beads. In this way, the bead holding plate 2 that retains a plurality of probe-immobilized beads 5 in which each kind of the probes is correlated with the position of the wells 1 can be prepared. In the present example, n kinds of biomolecular probes are prepared, and No. 1 biomolecular probe is introduced into m wells in the first row, No. 2 biomolecular probe into m wells in the second row, and so on, and No. n biomolecular probe is introduced into m wells in the n-th row, thereby immobilizing the probes on the beads 3 held in each well 1. When the probes immobilized on the beads 3 on the bead holding plate 2 are relatively chemically stable biomolecules such as DNA, the prepared bead holding plate 2 can be stored in a desiccator or a refrigerator, thus allowing its preparation to be conducted in bulk. The bead holding plate 2 in which a solution such as pure water is introduced into each well 1 is mounted on a device for capturing beads one by one and a stage for bead holding plate 6 of an apparatus for arraying beads as described later.

Figure 2:
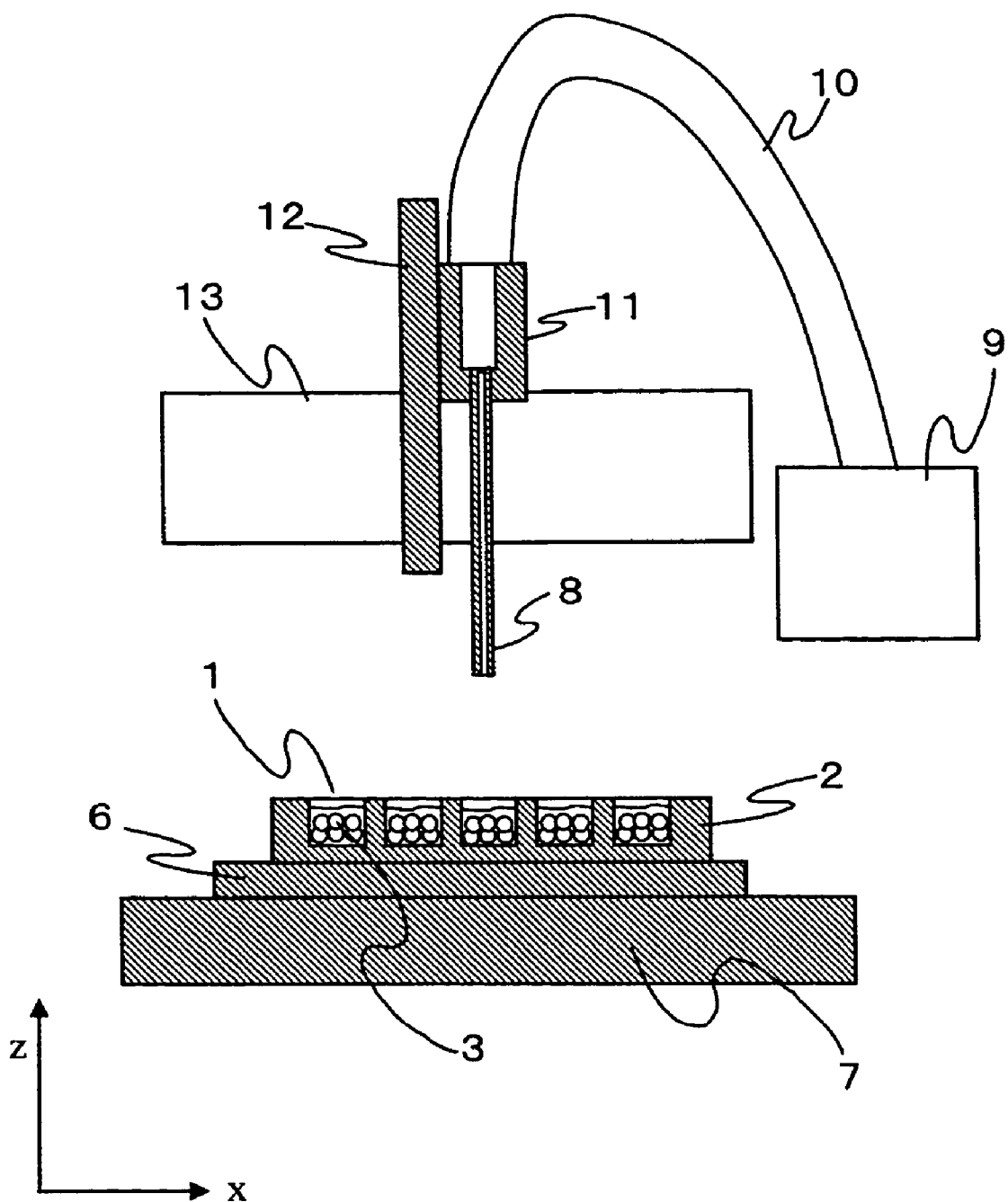
FIG. 2 is a schematic diagram explaining a device for capturing beads one by one according to the present invention.
Figure 4:
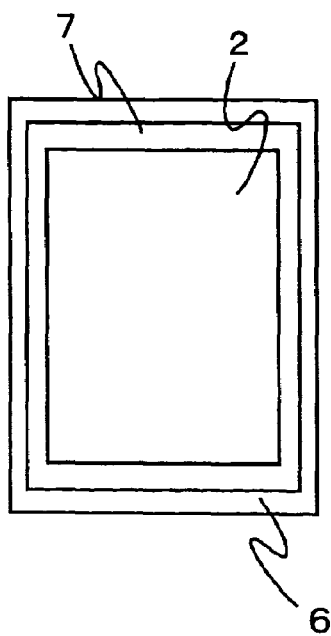
FIGS. 4A to 4F are diagrams explaining a circular vibration of the bead holding plate.
Figure 4:
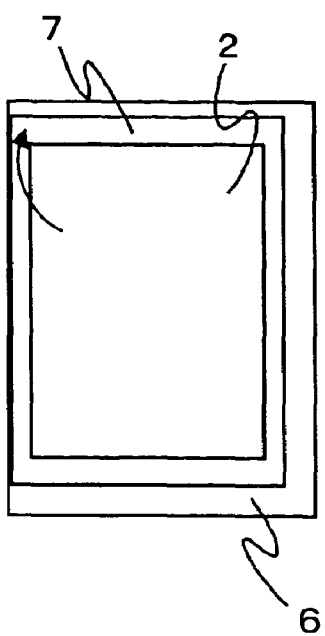
Figure 4:
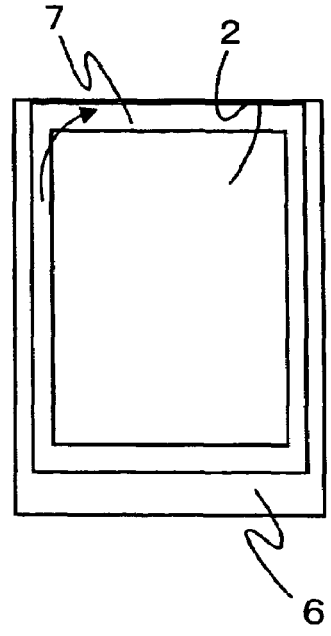
Figure 4:
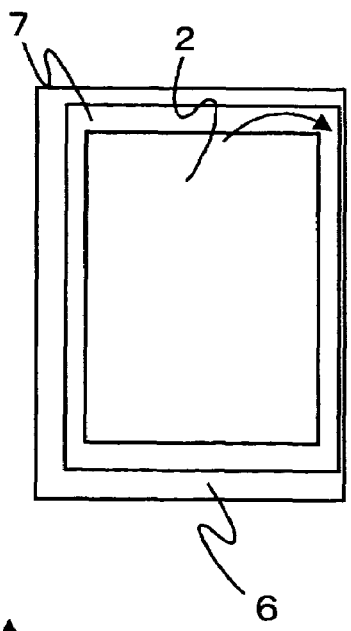
Figure 4:
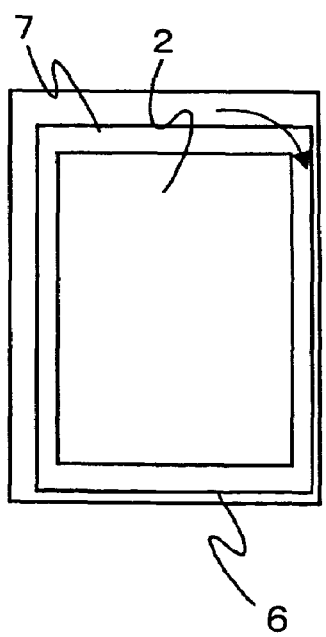
Figure 4:
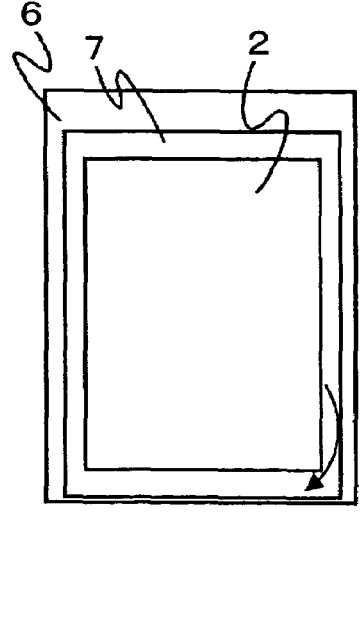

FIG. 2 is a schematic diagram explaining an example of the device for capturing beads one by one according to the present invention. This device for capturing beads one by one is provided with a vibration generator 7 mounted with the stage for bead holding plate 6 where the bead holding plate 2 is arranged, a bead capturing nozzle 8, a suction pump 9, a first electric actuator 12 to drive the bead capturing nozzle 8 in the z direction, and a second electric actuator 13 to drive the bead capturing nozzle 8 in the xy directions. The bead capturing nozzle 8 is retained by a bead capturing nozzle retaining member 11 fixed on the electric actuator 12 and connected to the suction pump via a tube 10. The vibration generator 7 can be varied in vibration amplitude and vibration frequency. The structure of the apparatus for arraying beads provided with the device for capturing beads one by one is described later.

The vibration generator 7 vibrates the bead holding plate 2 by moving the stage for bead holding plate 6 in the direction of the x axis or the y axis as shown in FIGS. 3A to 3C. FIGS. 3A to 3C show a case where vibration is generated in a reciprocating motion in the direction of the x axis. The vibration generator 7 may be driven in a circular motion of the bead holding plate 2 centered at a certain base point as shown in FIGS. 4A to 4F. Further, the amplitude of the vibration may be given in the direction of the z axis. However, when the bead holding plate 2 is vibrated in the direction of the z axis, a solution contained in the well 1 tend to overflow, and there is a risk that the bead capturing nozzle 8 and the bottom of the well 1 collide with each other, therefore rendering it undesirable in view of safe operation of the apparatus. Further, the vibration may also be given to the bead capturing nozzle 8. However, accuracy of positioning by the bead capturing nozzle retaining member 11 and reproducibility of positioning of the tip of the bead capturing nozzle 8 deteriorate, rendering it undesirable in view of safe operation of the apparatus.

FIGS. 14A and 14B show the shapes of the bead capturing nozzle 8 schematically. FIG. 14A shows a typical shape of the bead capturing nozzle 8 having uniform inner and outer diameters from the tip to the end, and the bead capturing nozzle of this structure can make use of a commercially available capillary. FIG. 14B shows a shape of the bead capturing nozzle with its tip tapered, and the bead capturing nozzle of this structure can make use of a capillary for wire bonding that is used in semiconductor manufacturing. In addition, these nozzles can be fabricated by a semiconductor etching technique. The material used for the nozzle includes stainless steel, glass, ceramic, ruby, silicon, and the like. In the example below, a bead capturing nozzle having a flat tip shape as shown in FIG. 14A was used.

FIGS. 5A to 5E are schematic cross sectional views showing the steps of picking up only one bead 3 from a plurality of beads held in the well 1 together with a solution 14 with the use of the device for capturing beads one by one shown in FIG. 2. The solution 14 here is pure water.

Figure 5:
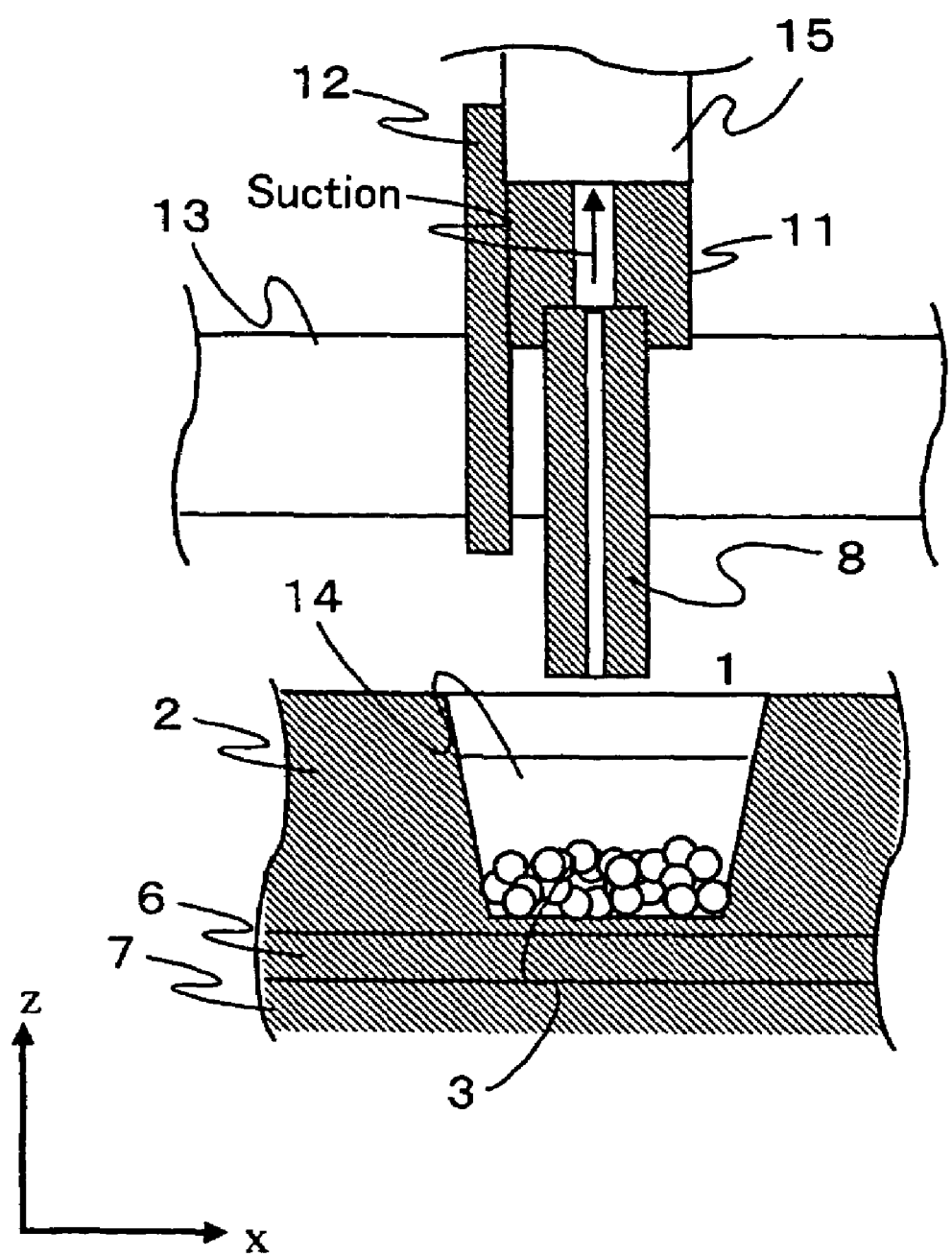
FIG. 5A is a schematic diagram showing a state just before a bead capturing nozzle is inserted into a well.
FIG. 5B is a schematic diagram showing a state that the bead capturing nozzle is inserted into the well.
FIG. 5C is a schematic diagram showing a state that a vibration is applied to the well.
FIG. 5D is a schematic diagram showing a state of the moment when the bead capturing nozzle is separated from a group of settling beads.
FIG. 5E is a schematic diagram showing a state that the bead capturing nozzle is withdrawn outside of the well.
Figure 5:
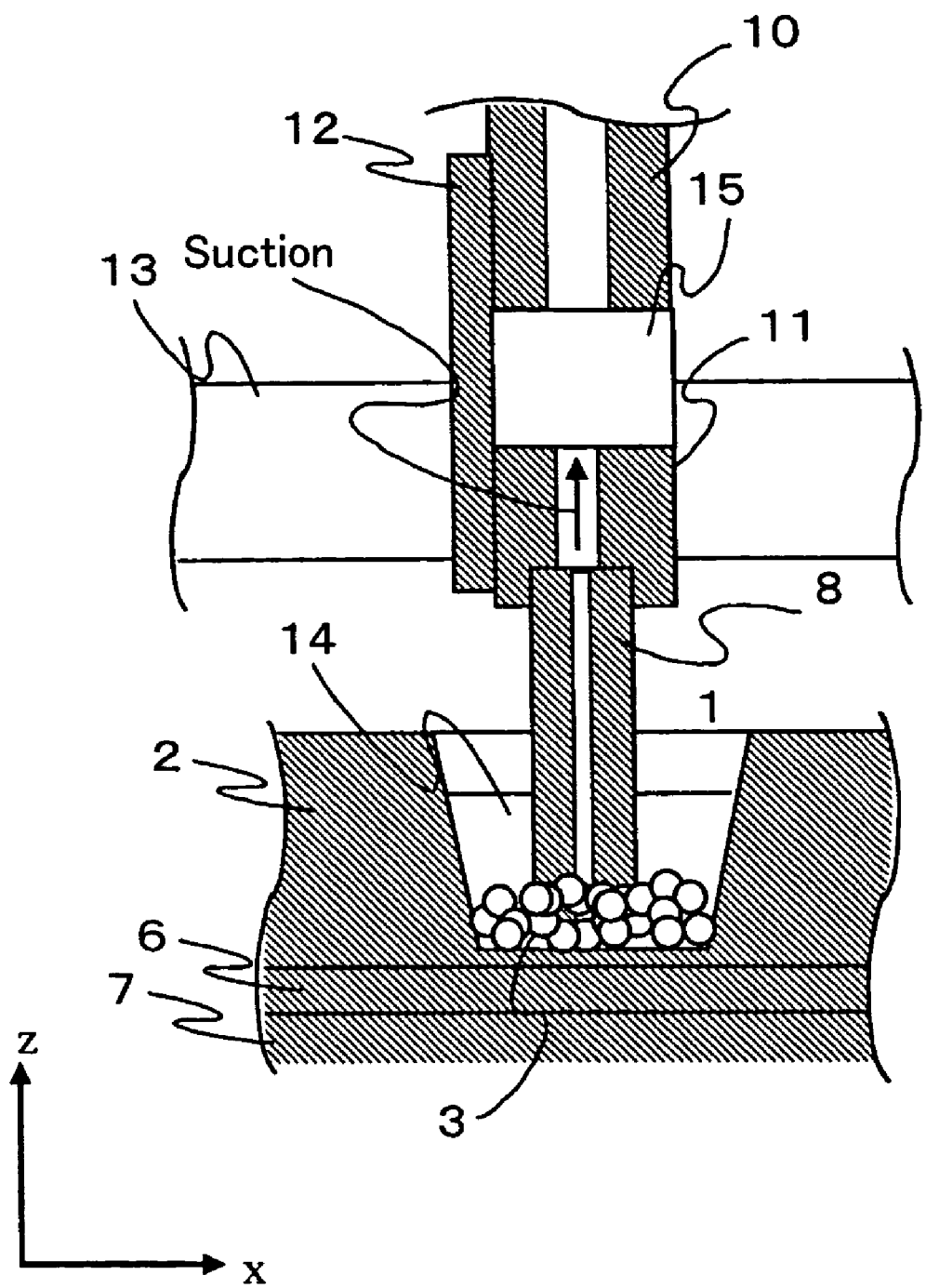
Figure 5:
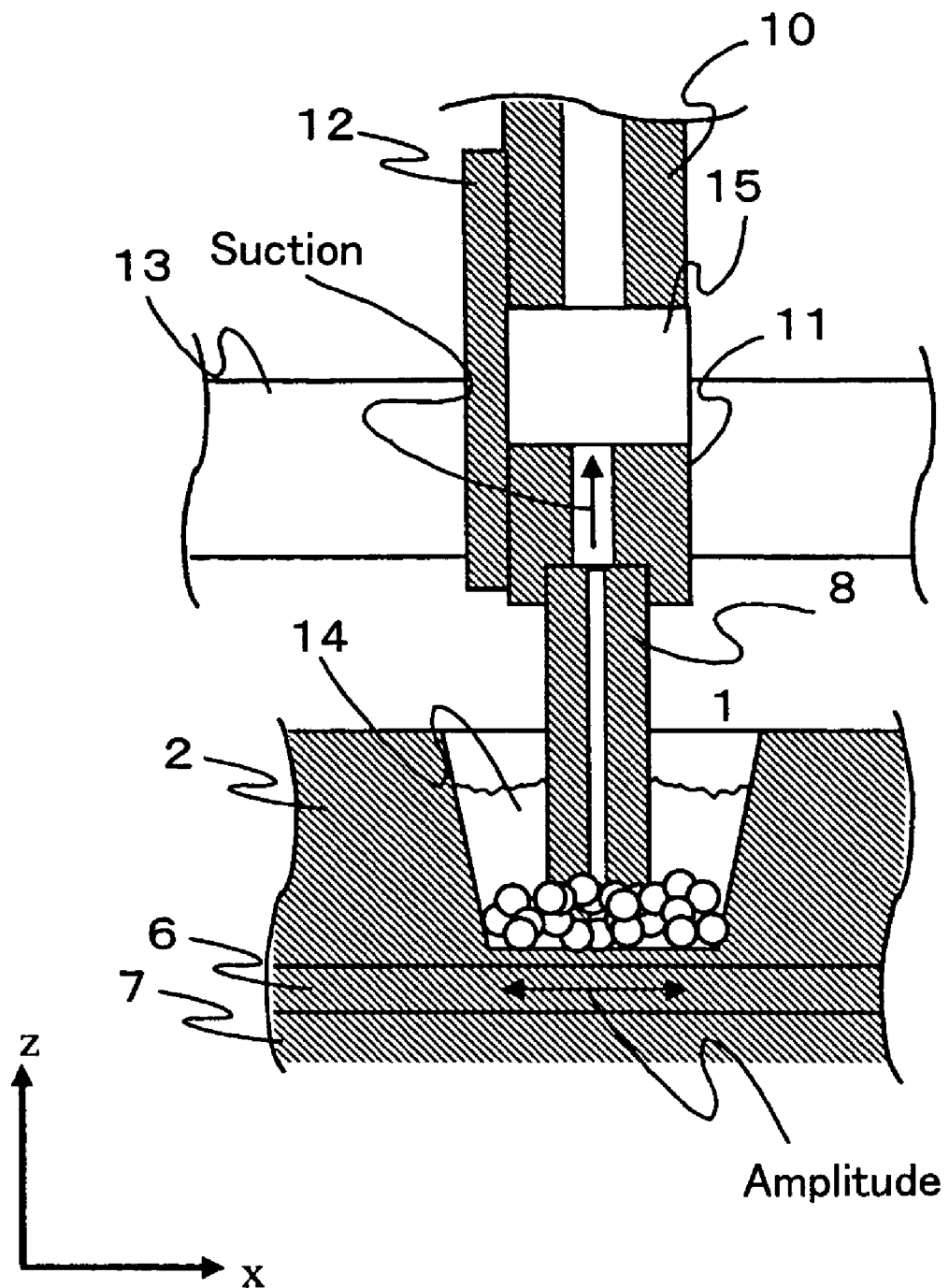
Figure 5:
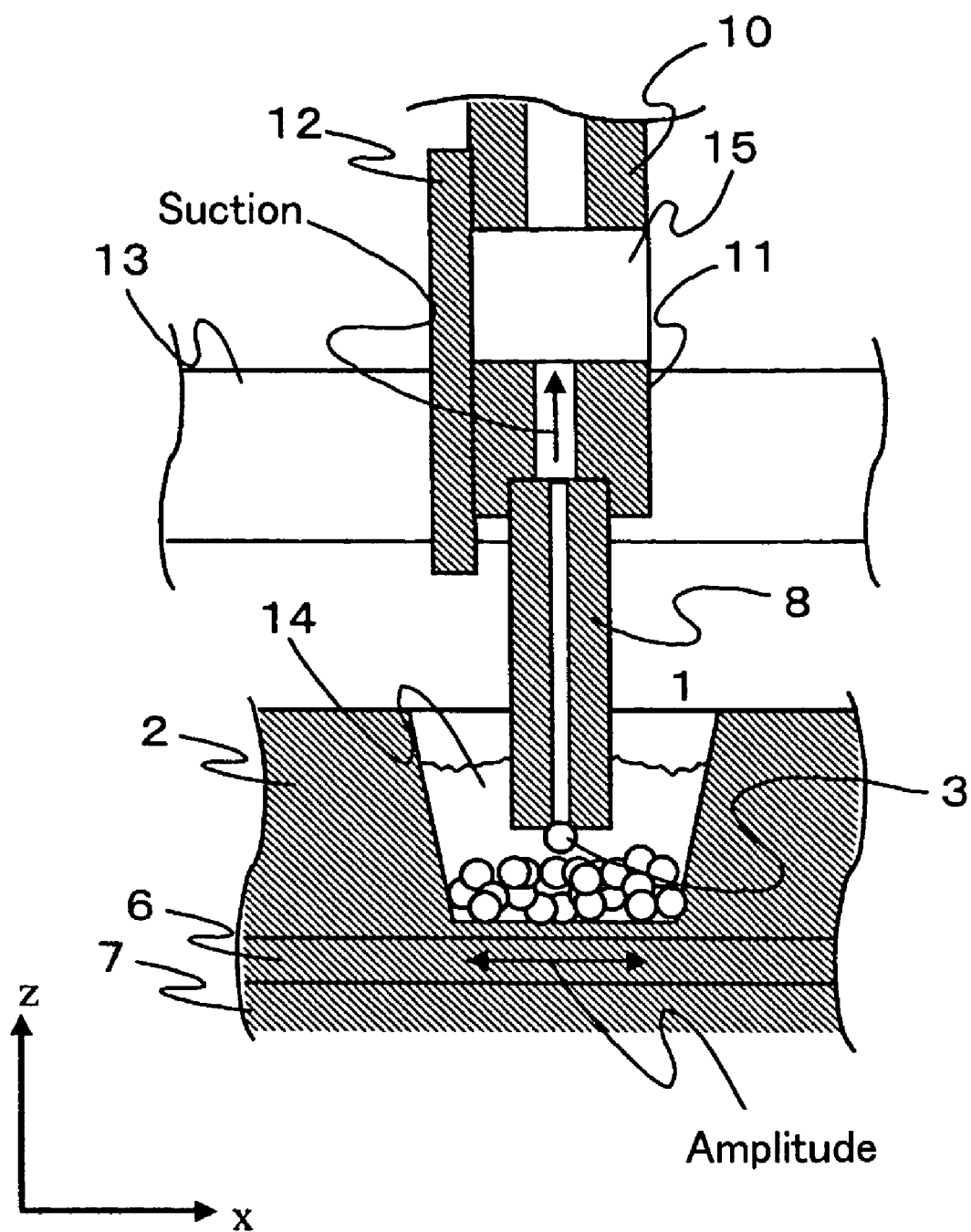
Figure 5:
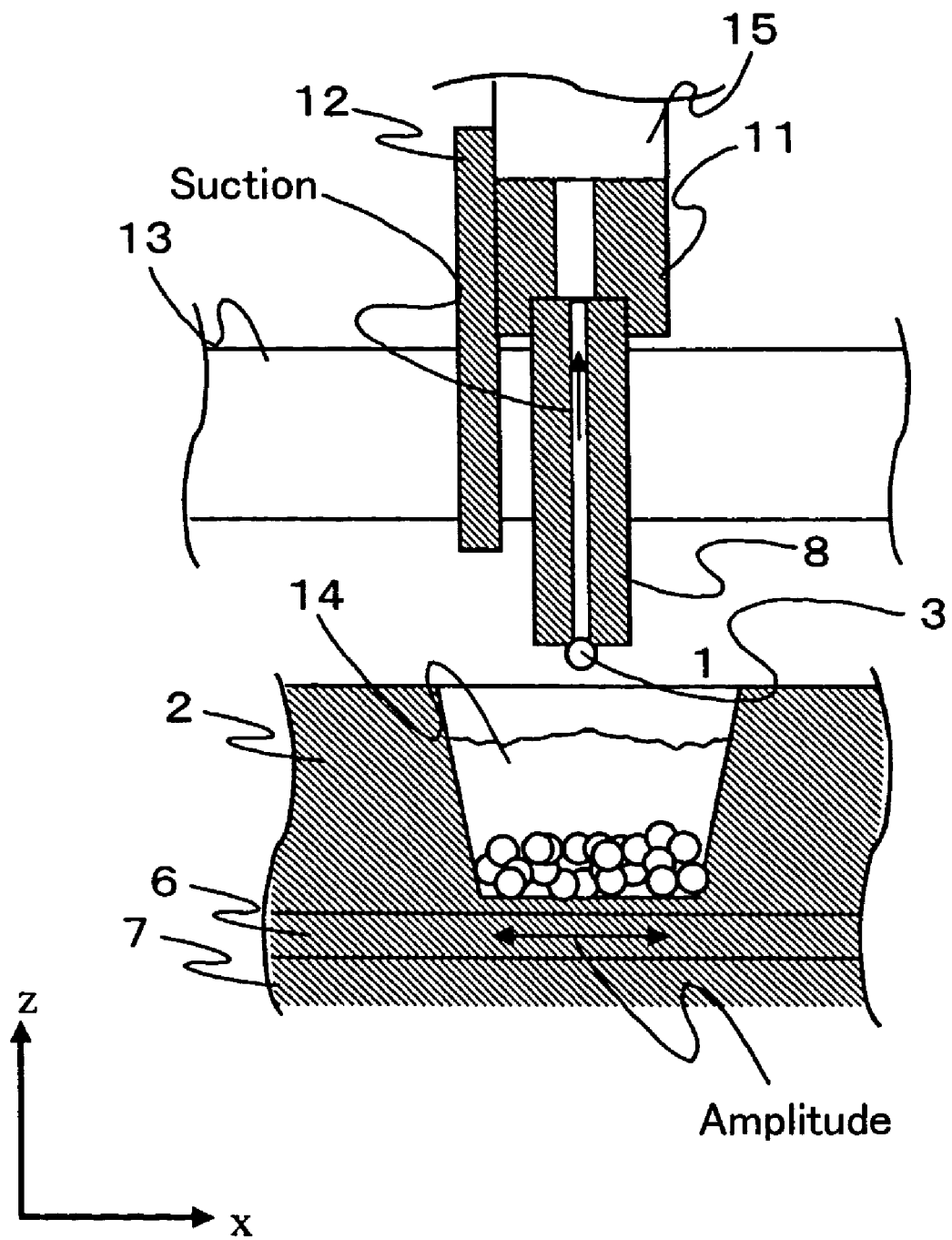

FIG. 5A depicts a state that the bead capturing nozzle 8 is moved by the second electric actuator 13 such that the opening of the well 1 retaining target beads 3 is set at a position opposite to the opening of the bead capturing nozzle 8 in the z direction. The figure shows a state that the bead capturing nozzle 8 is just about to be inserted into the target well 1. At this time, the suction pump 9 connected to the bead capturing nozzle 8 is driven, and a negative pressure is created at the tip of the bead capturing nozzle 8. Alternatively, the suction pump 9 is kept driven at all times, an electromagnetic valve 15 is inserted between the bead capturing nozzle 8 and the suction pump 9 in advance, and the electromagnetic valve 15 may be controlled by switching.

FIG. 5B depicts a state that the bead capturing nozzle retaining member 11 descends in the z direction by the control of the first electric actuator 12 and the lower tip of the bead capturing nozzle 8 in which a negative pressure is created is inserted into the inside of the well 1. The distance between the tip surface of the bead capturing nozzle 8 and the bottom of the well 1 is adjusted appropriately so as to make contact with each other in the inserted state. This is because a decrease of efficiency of bead capturing caused by inaccessibility of the tip of the bead capturing nozzle 8 to the bead 3 is prevented when the content of the beads 3 is low.

FIG. 5C depicts a state that the vibration generator 7 is driven and the bead holding plate 2 is vibrated at a predetermined frequency and predetermined amplitude. The figure depicts a state that the bead holding plate 2 is vibrated only in the direction of the x axis. The extent of the vibration to be given is sufficient if the surface of the solution 14 is shaken. It is unnecessary for the beads 3 to be stirred. In other words, it is a state that a certain vibration is given to the entire group of the precipitated beads. The upper and lower limits of the frequency and amplitude provided here are described later based on the experimental result in FIG. 6. Although the vibration generator 7 is driven after the bead capturing nozzle 8 is inserted in FIG. 5C, the vibration generator 7 may be kept driven from the time point in FIG. 5A.

FIG. 5D depicts the right moment at which the bead capturing nozzle 8 leaves the group of beads settling at the bottom of the well 1. At this time, only one bead 3 is captured at the tip of the nozzle. When the amplitude is generated at a frequency below the lower limit described later, a plurality of the beads 3 are attached to the tip surface. In addition, the beads 3 are also adsorbed on the sidewall of the bead capturing nozzle 8.

FIG. 5E depicts a state that the bead capturing nozzle 8 is moved to the z direction farther than the state in FIG. 5D where the tip of the bead capturing nozzle 8 passes through the interface between the solution 14 and the air and is withdrawn completely into the air.

According to the steps explained by FIGS. 5A to 5E, one bead 3 is retained at the tip of the bead capturing nozzle 8 without fail.

First Embodiment

Figure 6:
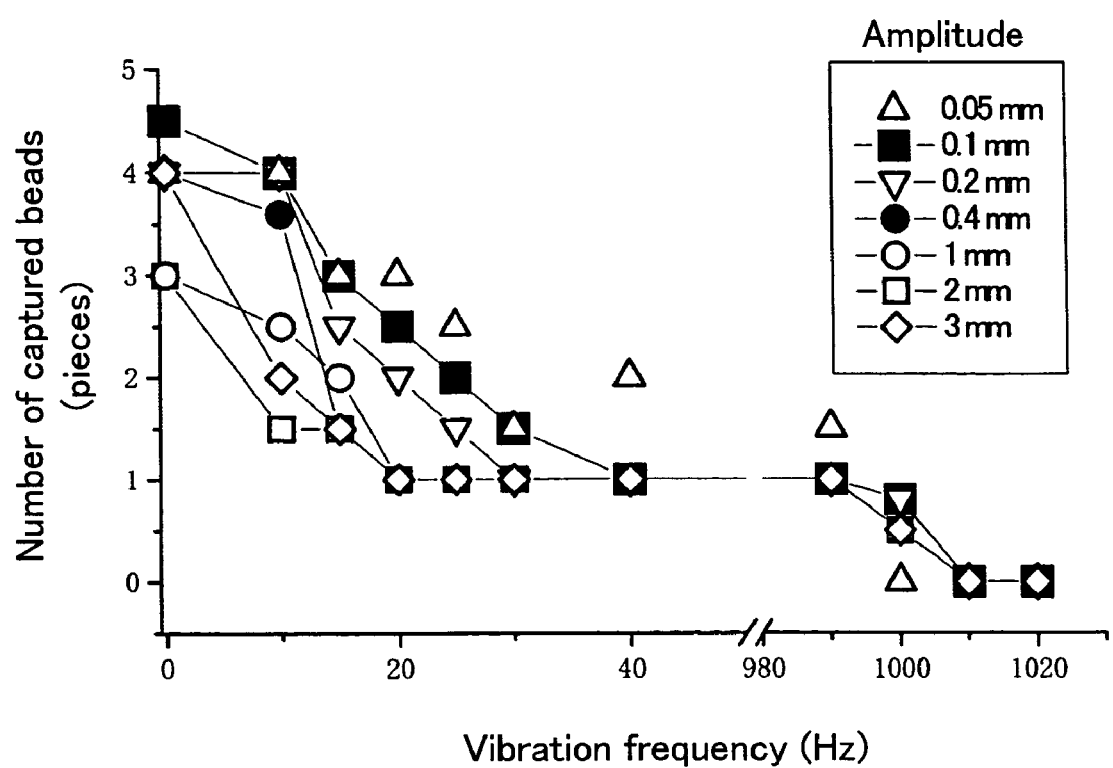
FIG. 6 is a graph showing a relation between the number of captured beads and vibration frequency.

FIG. 6 depicts the relation between the vibration frequency and the number of captured beads 3, showing how the beads were captured when the frequency and amplitude for vibration in the direction of the x axis in FIG. 5C were varied. In this experiment, the beads having a diameter of 0.1 mm and the bead capturing nozzle 8 having an inner diameter and outer diameter of 0.05 mm and 0.4 mm, respectively, were used. For the wells 1, wells of a 384-well microtiter plate having an opening diameter of 3.5 mm were used. Three milligrams of the beads 3 were introduced into each well 1 using a spatula, followed by addition of 60 microliters of pure water 14. The operation of bead capture was repeated ten times for every frequency, and the average number of the captured beads was determined and plotted.

FIG. 6 shows that a smaller amplitude is sufficient as the frequency becomes higher. However, when the amplitude was smaller than 0.1 mm, it was not possible to capture only one bead 3 even when the frequency was increased as shown in FIG. 6. Hence, it can be said that a frequency equal to or higher than 20 Hz and amplitude equal to or larger than 0.1 mm are lower limits required for capturing a single bead. Further, it is shown that a single bead could be captured without fail by applying a frequency equal to or higher than 20 Hz in the range of the amplitude equal to or larger than 0.4 mm. This result indicates that only one bead 3 can be captured at an approximate frequency of 20 Hz when an amplitude equal to or larger than the outer diameter of the nozzle is provided.

When the vibration frequency was equal to or higher than 1,000 Hz, it was found difficult to capture the bead 3 at any amplitude. However, it is expected to be able to capture the bead even at a frequency equal to or higher than 1,000 Hz when changes such as decreasing flow resistance in the suction path and enhancing flow rate by means of increasing the inner diameter and further the inner diameter other than the tip are carried out in the inner structure of the bead capturing nozzle 8. Although the amplitude was changed only up to 3 mm because of the size of the well 1, it is evident from this result that the bead can be captured even when the amplitude is larger than 3 mm.

Although it was possible to control the beads in a range of amplitude from 0.1 mm to 3 mm, a load is applied to the bead capturing nozzle 8 when a large amplitude is given while the bead capturing nozzle is inserted into the group of beads, and thus there is a possibility that the tip may be distorted or may further be broken. Therefore, it is better to set the amplitude small.

Figure 7:
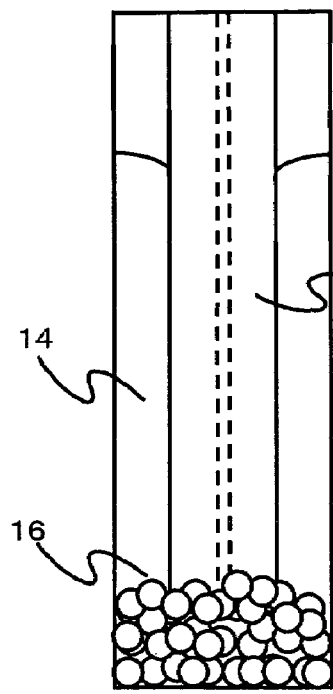
FIGS. 7A to 7C are schematic diagrams explaining a set of continuous microphotographs showing a process of bead capture, where
Figure 7:
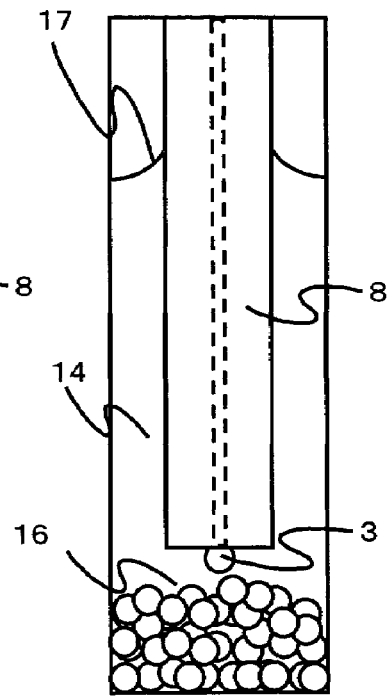
Figure 7:
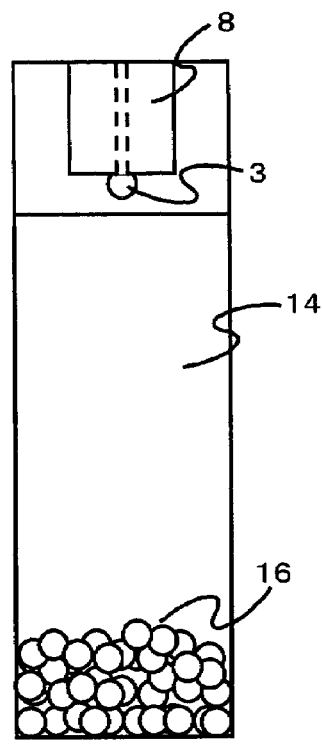
Figure 8:
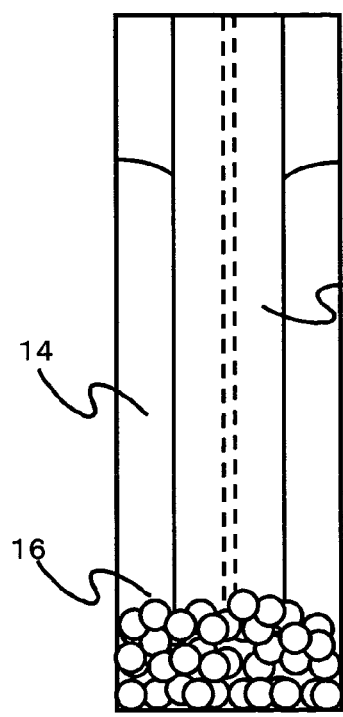
FIGS. 8A to 8C are schematic diagrams explaining another set of continuous microphotographs showing the process of bead capture, where
Figure 8:
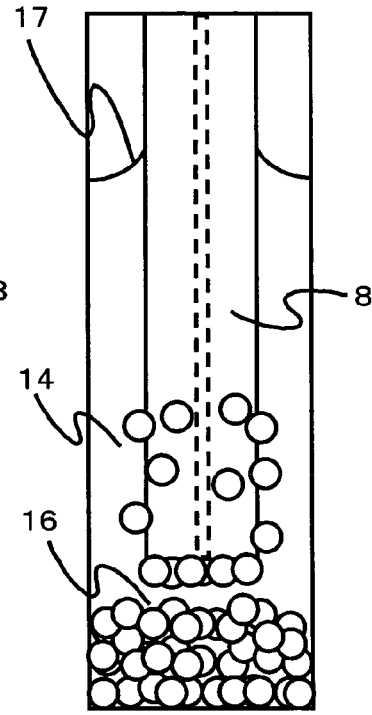
Figure 8:
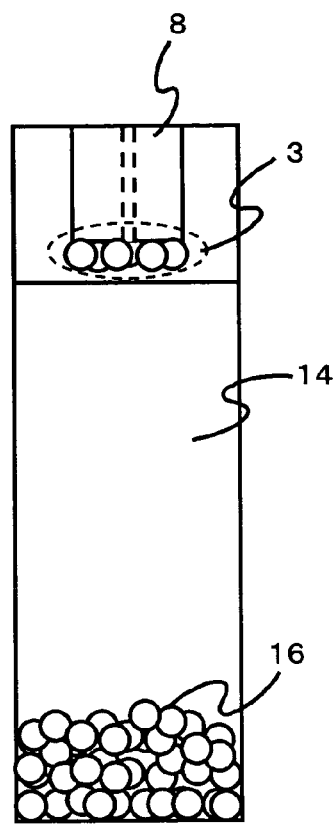

FIGS. 7 and 8 are images showing bead capture by the use of the device for capturing beads one by one of the present invention. FIGS. 7A to 7C represent part of continuous microphotographic diagrams showing a process of the bead capture when vibration is provided by the vibration generator 7. The condition of the vibration consisted of a frequency of 20 Hz and an amplitude of 0.4 mm. FIG. 7A is a microphotographic diagram showing a state that the bead capturing nozzle 8 in which a negative pressure was created was inserted into a group of beads 16 in the well 1. FIG. 7B is a microphotographic diagram showing the moment when the bead capturing nozzle 8 was separated from the group of beads 16 settling at the bottom of the well 1. It is seen that only one bead 3 was captured exclusively at the tip of the bead capturing nozzle 8 at this time point. FIG. 7C is a microphotographic diagram showing a state that the tip of the bead capturing nozzle 8 was withdrawn into the air. It is seen that only one bead 3 was captured at the tip of the bead capturing nozzle 8 even after passing through the air-liquid interface.

FIGS. 8A to 8C represent part of continuous microphotographic diagrams showing a result of the bead capture when the vibration frequency provided by the vibration generator 7 was lower than 20 Hz. The condition of the vibration consisted of a frequency of 10 Hz and an amplitude of 0.3 mm. FIG. 8A is a microphotographic diagram showing a state that the bead capturing nozzle 8 in which a negative pressure was formed was inserted into the group of beads 16 in the well 1. FIG. 8B is a microphotographic diagram showing the moment when the bead capturing nozzle 8 was separated from the group of beads 16 settling at the bottom of the well 1. It is seen from FIG. 8B that a plurality of the beads were attached to the side surface and portions of the tip surface other than the suction portion of the bead capturing nozzle 8 in the solution 14. FIG. 8C is a microphotographic diagram showing a state that the tip of the bead capturing nozzle 8 was withdrawn into the air. It is seen that the beads on the side surface were removed by the surface tension of an air-liquid interface 17 as the result of withdrawing the bead capturing nozzle 8 into the air, while extra beads 3 remained sticking to the tip surface.

The results in FIGS. 7 and 8 indicate that only one bead 3 can be adsorbed and captured at the tip of the bead capturing nozzle 8 from the group of beads 16 by applying an appropriate vibration to a chamber, i.e. the well 1, containing the beads and the solution.

Second Embodiment

FIGS. 9A and 9B are schematic diagrams showing a structure of an apparatus for arraying beads provided with the device for capturing beads one by one according to the present invention, where FIG. 9A is a perspective view and FIG. 9B is a cross sectional view. The vibration generator 7 and the stage for bead holding plate 6 constituting the device for capturing beads one by one of the present invention were placed on a plate-like base 18, and the bead capturing nozzles 8 retained by the bead capturing nozzle retaining member 11 was arranged above the stage 6. The bead capturing nozzle 8 was connected to a vacuum/pressure pump 23. The bead capturing nozzle retaining member 11 was driven by the first electric actuator 12 and the second electric actuator 13. The base 18 was provided with through-holes for movement assistance 19, and a first image sensor 20, a second image sensor 21, and a suction pump for introducing beads 22 were arranged. The numeral 24 represents a control computer.

The details of the device for capturing beads one by one have been explained in FIGS. 1 to 4. In the present embodiment, a structure having an arrangement of a plurality of the bead capturing nozzles 8 was employed, and n pieces of the bead capturing nozzles 8 were provided in parallel with the direction of the y axis at the same spacing as that for the wells 1 on the bead holding plate 2. The number of the bead capturing nozzles 8 was five in the illustrated example. When a microtiter plate having the wells 1 of a diameter of 3.5 mm and a depth of 9.6 mm arranged in a total of 384, 24 (m=24) in the direction of the x axis and 16 in the direction of the y axis (n=16), is used, it is desirable to arrange 16 bead capturing nozzles 8 in parallel with the direction of the y axis. The positions of the tips of the bead capturing nozzles 8 were aligned in the direction of the z axis and these were firmly retained by the bead capturing nozzle retaining member 11 so as to be handled as a group. The bead capturing nozzles were connected to the vacuum/pressure pump 23 capable of aspirating as well as pressurizing. The suction and pressurization can be arbitrarily selected by switching a valve.

The through-holes for movement assistance 19 were provided in n pieces in parallel with and at the same spacing as that for the wells 1 arranged in the direction of the y axis of the bead holding plate 2. The cross section of the through-hole for movement assistance 19 is circular and has a central axis parallel to the z axis. Since the through-holes for movement assistance 19 were provided to support insertion of the beads 3 adsorbed on the tip openings of the bead capturing nozzles 8 into capillaries for bead array 25 while guiding a plurality of the bead capturing nozzles 8 and the capillaries for bead array 25, the inner diameter of the through-holes for movement assistance 19 is designed such that the capillary for bead array 25 and the bead capturing nozzle 8 can move safely. For example, when the bead capturing nozzle 8 has an outer diameter of 0.4 mm and an inner diameter of 0.05 mm, the inner diameter of the through-hole for movement assistance 19 is set to 0.5 mm.

The first image sensor 20 was placed at a location parallel and adjacent to the through-holes for movement assistance 19. This image sensor 20 was used to confirm whether the beads 3 were captured at the tips of the bead capturing nozzles 8 one by one before the bead capturing nozzles 8 were introduced into the through-holes for movement assistance 19. When it was found from an output of the first image sensor 20 that there was any bead capturing nozzle 8 on which the bead 3 was not captured, the operation of bead capture by the bead capturing nozzle 8 was repeated.

The second image sensor 21 was placed at a location opposite to the first image sensor 20 and on the undersurface side of the base 18 and used to confirm whether the beads 3 were introduced into the capillaries for bead array 25.

The capillaries for bead array 25 were provided in n pieces in parallel with the direction of the y axis at the same spacing as that for the wells 1 on the bead holding plate 2 and also corresponded to the bead capturing nozzles 8. Although the number of the capillaries for bead array 25 was five in the illustrated example, sixteen of these are arranged in parallel with the direction of the y axis in the structure of the above example with the titer plate. One end of the capillary for bead array 25 had an opening, and the other end was connected to the suction pump for introducing beads 22 via a tube1and aspirated. It is desirable that the end portion of the capillary for bead array 25 and the tube are connected via a socket 26. Here, the socket 26 had an inner diameter smaller than the outer diameter of the beads 3 so as to prevent the passage of the beads 3.

With the use of the apparatus for arraying beads, the beads 3 were aspirated into the capillaries for bead array 25 one by one, and a plurality of the beads 3 were arrayed therein while keeping the order of the beads that had been aspirated.

When the diameter of the bead 3 is R, the inner diameter ID of the capillary for bead array 25 satisfies the relation of R<ID<2R. When the diameter of the bead 3 is 0.1 mm, the inner diameter and outer diameter of the capillary for bead array 25 may be set to 0.15 mm and 0.38 mm, respectively.

It is advisable that the end portions on the opening side of the capillaries for bead array 25 are retained by a holder 27 in a firmly fixed manner so that the tip portions of the capillaries for bead array 25 may be aligned in the direction of the z axis and they are handled as a group. Of course, it is advisable that the capillaries for bead array 25 may be released from being retained by the holder 27 and may be treated as individual capillaries for bead array 25 after necessary beads 3 have been inserted into them.

After the beads 3 had been adsorbed to the tip openings of the bead capturing nozzles 8 via the operation process for the device for capturing beads one by one explained by the use of FIGS. 1 and 2, the bead capturing nozzles 8 were moved by the first electric actuator 12 and the second electric actuator 13, and the tip openings of the bead capturing nozzles 8 and the openings of the capillaries for bead array 25 were allowed to be opposite to each other within the through-holes for movement assistance 19. Then, the tubes connected to the bead capturing nozzle 8 were pressurized to release the beads adsorbed to the tip openings, thereby allowing the beads to be transferred into the capillaries for bead array 25. At this time, the beads 3 were effectively introduced into the capillaries for bead array 25 by aspirating the inside of the capillaries for bead array 25.

Figure 10:
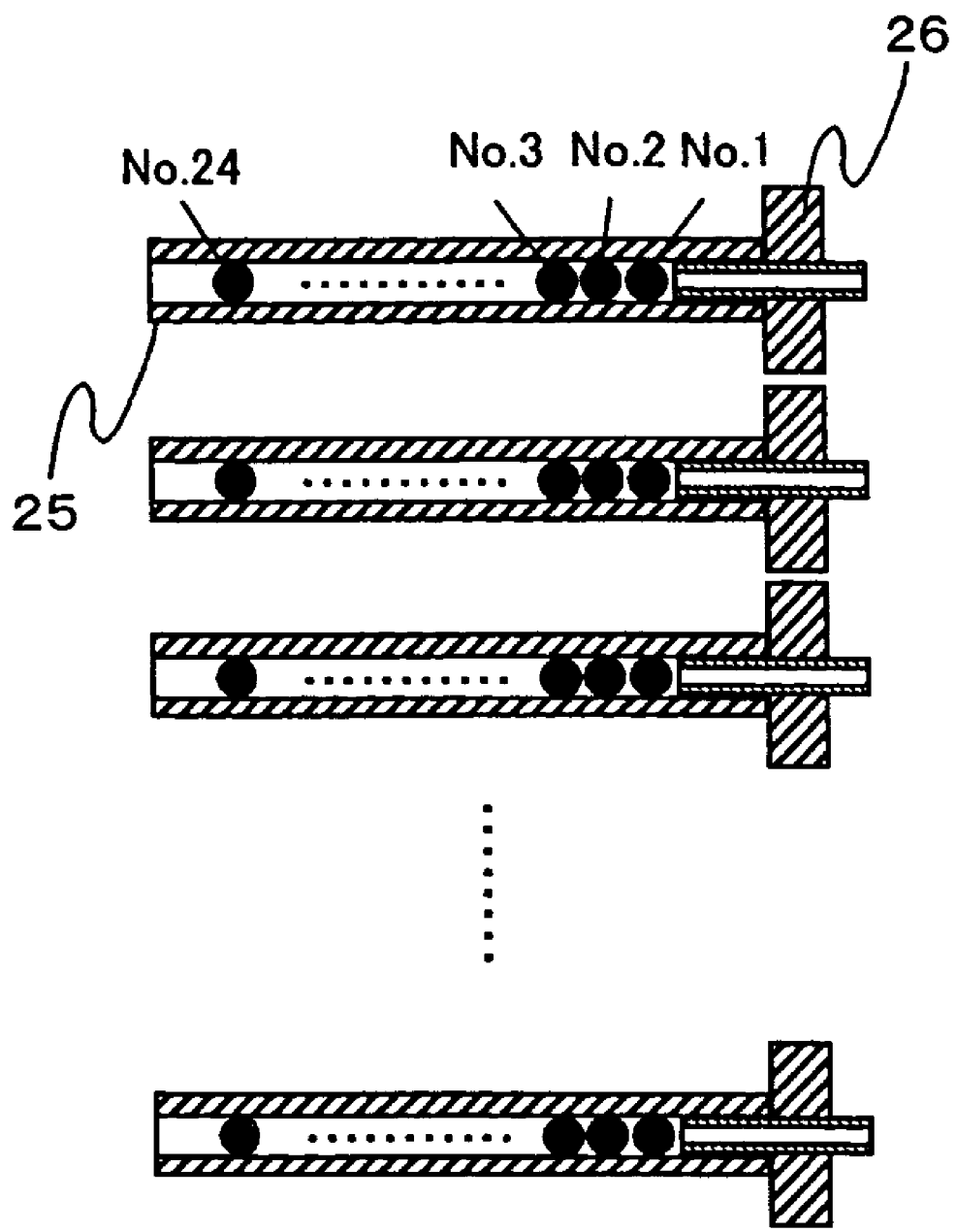
FIG. 10 is a schematic diagram showing a plurality of bead arrays prepared by the use of the apparatus for arraying beads of the present invention.

FIG. 10 is a schematic cross sectional view of an example of a plurality of the capillaries for bead array 25 obtained by the use of the bead holding plate 2 having m×n wells 1 according to the present embodiment. At this stage, narrow hollow tubes having an outer diameter approximately equal to the inner diameter of the capillary were inserted into both ends of the capillary so that the beads 3 introduced into the capillary might not drop out and be kept in an orderly arrayed state, thereby preventing any movement of the beads 3. However, the narrow hollow tube to be inserted into the left side is omitted in the illustrated example. This is because it is necessary to introduce a sample into the capillary for bead array 25.

Figure 9:
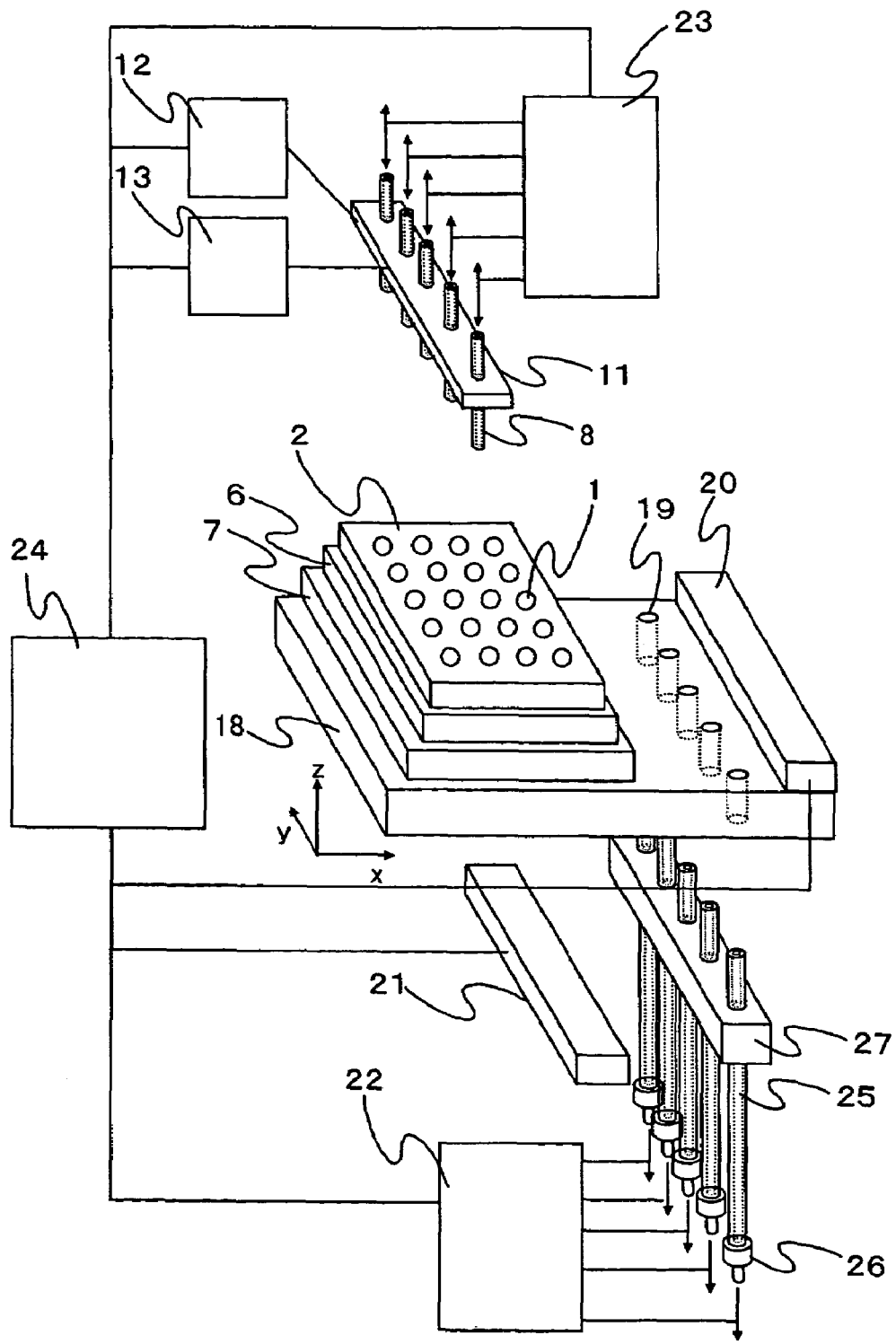
FIG. 9A is a schematic diagram showing a structure example of an apparatus for arraying beads according to the present invention.
FIG. 9B is a schematic cross sectional view showing the structure example of the apparatus for arraying beads according to the present invention.
Figure 9:
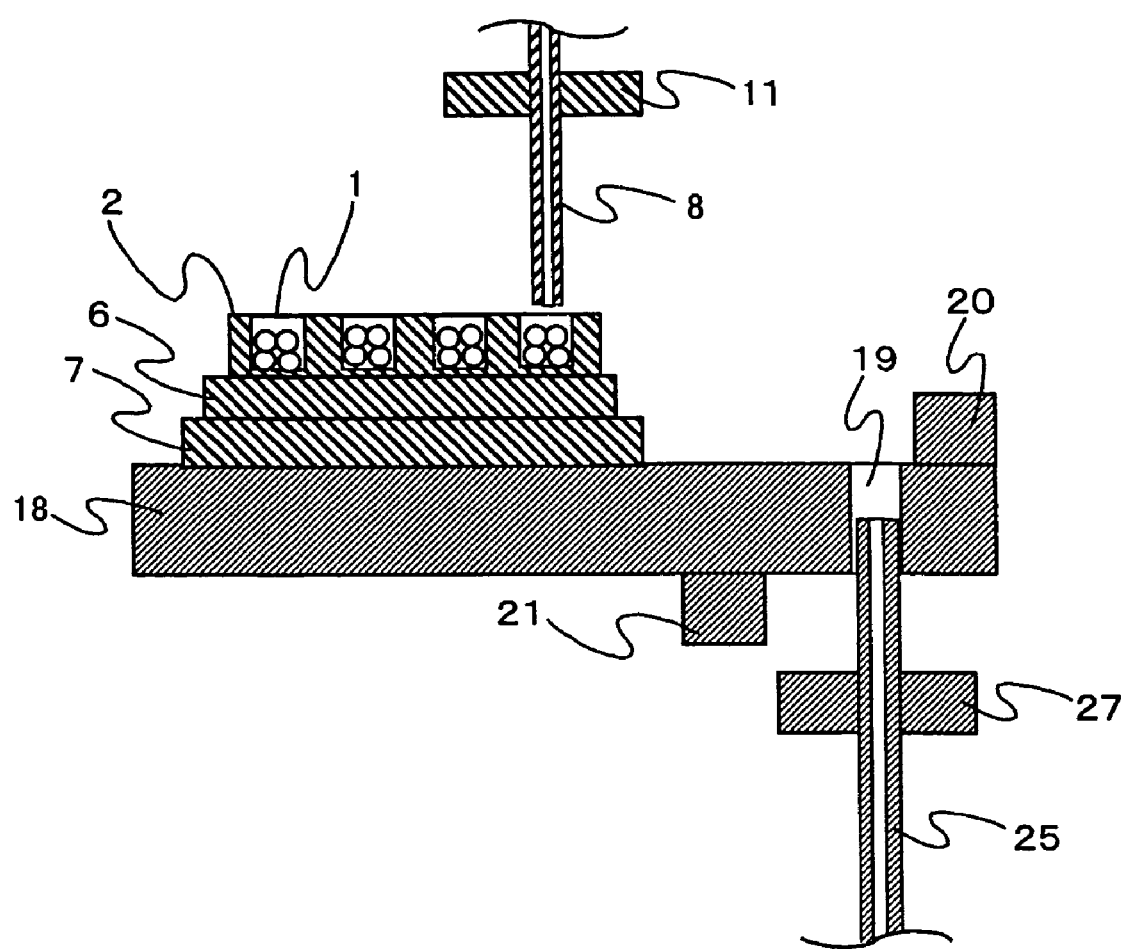

An example of the use of the capillaries for bead array in which fluorescently labeled specific target DNAs were hybridized to a DNA probe array that was prepared by arraying 24 kinds of DNA-immobilized beads attached with DNA probes one by one in an arbitrary order in the capillaries for bead array according to the example of the apparatus for arraying beads in FIG. 9 is explained with reference to FIGS. 11A and 11B.

Figure 11:
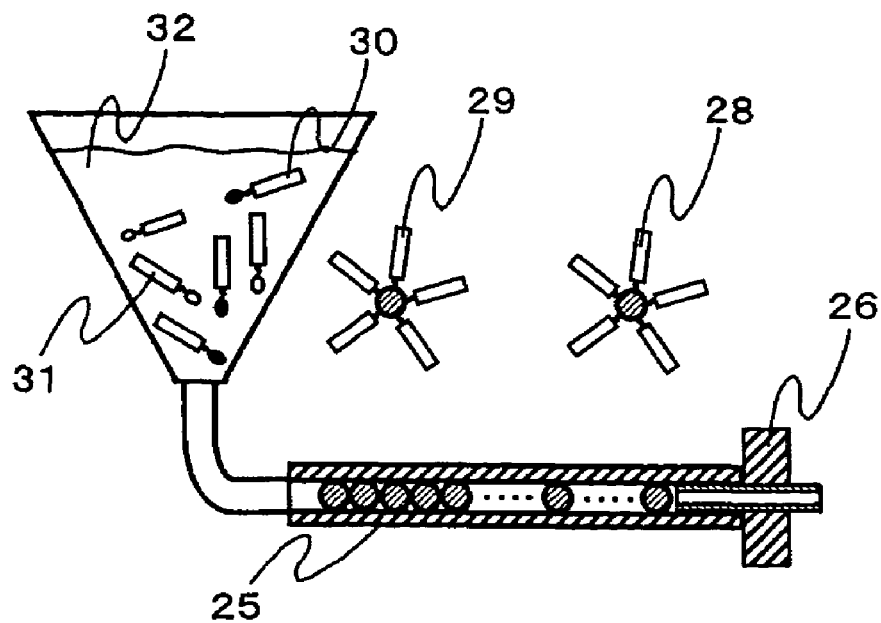
FIGS. 11A and 11B represent schematic diagrams showing a hybridization experiment, where
Figure 11:
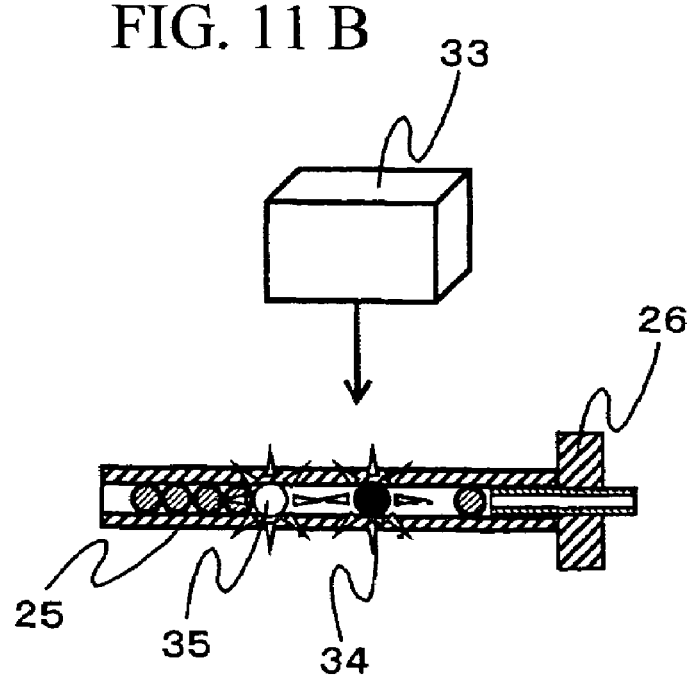

In FIGS. 11A and 11B, it was determined whether target DNAs bound to their corresponding probe DNAs as intended. For this purpose, 24 kinds of 18-mer synthetic oligonucleotides having each different sequence modified at the 5'-end by a thiol group were prepared as probes. Among the 24 kinds of the probes, the capillary for bead array 25 provided with both of a bead immobilized with a single stranded DNA probe 28 having Sequence 1 and a bead immobilized with a single stranded DNA probe 29 having Sequence 2 was allowed to come in contact with a flow of a sample containing a single stranded target DNA 30 having Sequence 3 complementary to Sequence 1 and labeled with Cy3 and a single stranded target DNA 30 having Sequence 4 complementary to Sequence 2 and labeled with TexasRed.

```
5'-thiol-ATCTGACT . . . GCTCCTC-3'      (Sequence 1)

5'-thiol-CTACCTGC . . . CTGGACG-3'      (Sequence 2)

5'-Cy3-GAGGAGCC . . . GTCAGAT-3'        (Sequence 3)

5'-TexasRed-CGTCCAGG . . . CAGGTAG-3'   (Sequence 4)
```

A solution of 20 mM phosphate buffer (pH 7.0) 32 containing the single stranded target DNA 30 and the single stranded target DNA 31 at a concentration of 1 µM respectively was flown into the capillary for bead array 25 with the prepared DNA probe array and subjected to hybridization at 45 degrees c. Feeding of the solution into the capillary was carried out with a syringe pump. After the reaction, the residual target DNA not involved in the hybridization reaction was washed successively with the 20 mM phosphate buffer (pH 7.0) solution 32 and pure water, followed by drying. Then, each bead in the capillary for bead array was observed by a fluorescent microscope 33 with a mercury lamp as light source using in turn a long-pass filter for Cy3 and a long-pass filter for TexasRed that were centered around emission wavelengths of Cy3 and TexasRed, respectively.

As the result, it was observed as shown in FIG. 11B that a specific bead generated fluorescence of Cy3 34 and another specific bead generated fluorescence of TexasRed 35, respectively, among the arrayed beads. This indicated that the single stranded target DNAs 30 and 31 specifically hybridized to the single stranded DNA probes 28 and 29, respectively. Thus, it was confirmed that, with the use of this apparatus for arraying beads, a DNA probe array can be prepared in the capillary for bead array 25 in an arbitrary linear arrangement without exerting an influence on probes.

Third Embodiment

Glass beads and plastic beads immobilized with biomolecular probes often exhibit variations in size. Further, the size of beads to be used differs depending on the difference in assay systems for genetic tasting. Here, a model experiment in which various beads having diameters larger than the diameter of the tip opening of the bead capturing nozzle 8 but equal to or smaller than its outer diameter were manipulated by one kind of bead capturing nozzle 8 is explained.

Figure 13:
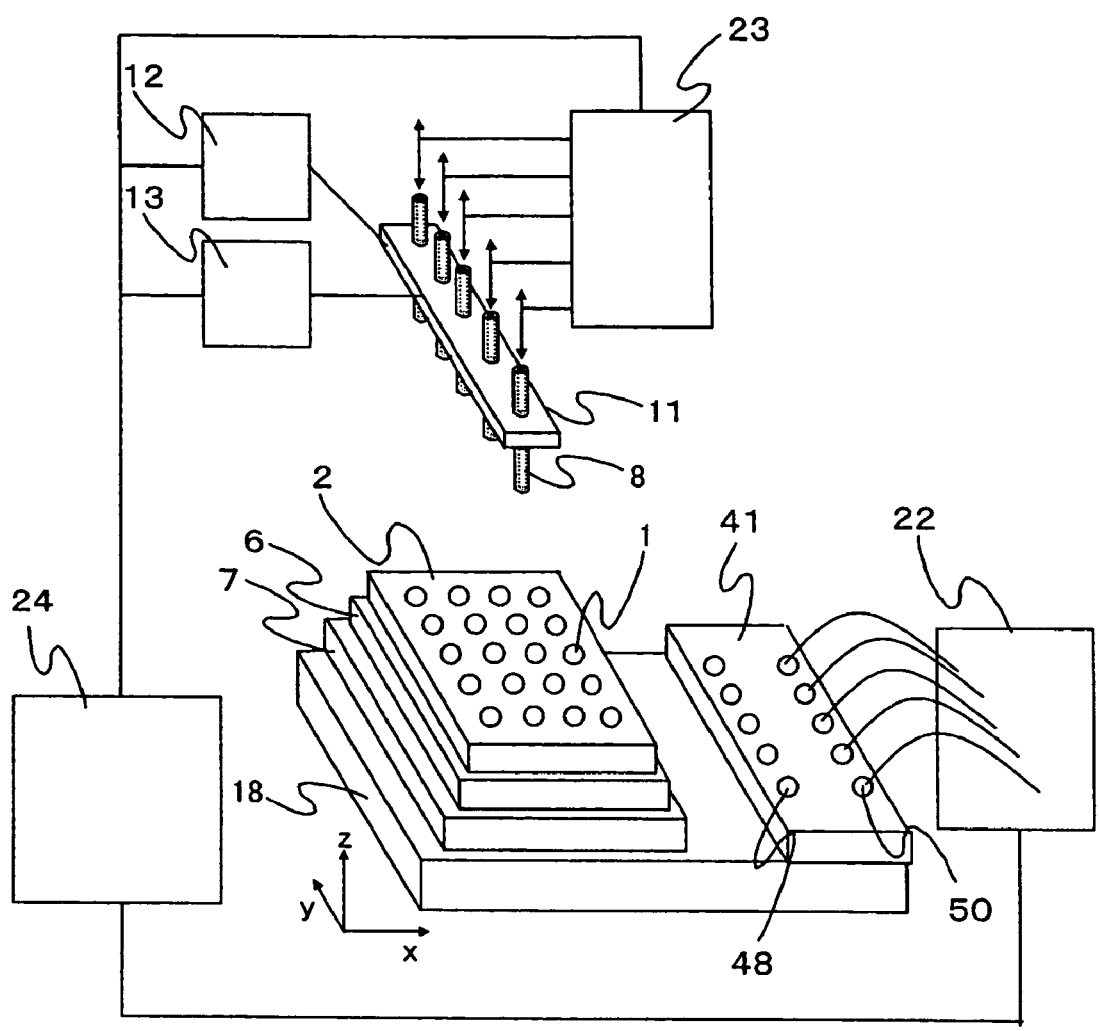
FIG. 13 is a schematic diagram showing a structure example of an apparatus for arraying beads on a chip according to the present invention.

In the experiment, beads of 0.05 mm 36, beads of 0.1 mm 37, beads of 0.3 mm 38, beads of 0.5 mm 39, and beads of 1 mm 39 were arrayed on a flow channel chip 41 having five different flow channel cross sections depending on each size of the beads using the apparatus for arraying beads shown in FIG. 13 in which the device for capturing beads one by one was mounted with the bead capturing nozzle 8 having an outer diameter of 1 mm and an inner diameter of 0.04 mm. FIG. 12A is a schematic diagram of the flow channel chip before arraying the beads, and FIG. 12B is a schematic diagram of the flow channel chip after arraying the beads.

The cross sectional shapes of the five flow channels on the chip may be either square or circular. In the present embodiment, a chip having flow channels in square cross section was used. Specifically, a chip 41 having five flow channels consisting of a square flow channel having a side of 0.07 mm 43, a square flow channel having a side of 0.13 mm 44, a square flow channel having a side of 0.35 mm 45, a square flow channel having a side of 0.6 mm 46, and a square flow channel having a side of 1.2 mm 47 was used. In each flow channel, a weir 48 was provided as a stopper for the beads, and the beads were introduced through a circular hole connected to the flow channel called a bead introduction inlet 49. The numeral 50 represents an opening for piping. When a bead array chip 42 was prepared, this opening was connected to a tube, and further to a suction pump, thereby aspirating the inside of the flow channel. That is, the beads can be introduced efficiently into the flow channel by the suction effect from the side of the opening for piping 50.

FIG. 13 is a schematic diagram showing a structure of an apparatus for arraying beads on a chip. Although its basic structure is similar to the apparatus shown in FIG. 9, it is structured such that the beads captured by the device for capturing beads one by one are introduced directly into bead introduction inlets 49 located at one ends of the flow channels of the flow channel chip 41 and further the side of the openings for piping 50 is connected to the suction pump for introducing beads 22 via tubes.

Five bead capturing nozzles 8 having an outer diameter of 1 mm and an inner diameter of 0.04 mm were arranged. For the bead holding plate 2, beads having the same diameter were placed in a row of the four rows in the direction of the x axis in FIG. 13, and beads having different diameters were placed in the five rows in the direction of the y axis in FIG. 13, respectively. One piece of the beads was taken out from each well in the direction of the m row one after another by the bead capturing nozzle 8 and introduced into the flow channel chip 41 having the five flow channels. The vibration condition of the device for capturing beads one by one was set to a vibration frequency of 20 Hz and amplitude of 1 mm.

A schematic diagram of a two-dimensional bead array chip 42 after arraying is shown in FIG. 12B. The beads having the diameter of 0.05 mm 36, the beads having the diameter of 0.1 mm 37, the beads having the diameter of 0.3 mm 38, the beads having the diameter of 0.5 mm 39, and the beads having the diameter of 1 mm 40 were arrayed in the square flow channel having the side of 0.07 mm 43, the square flow channel having the side of 0.13 mm 44, the square flow channel having the side of 0.35 mm 45, the square flow channel having the side of 0.6 mm 46, and the square flow channel having the side of 1.2 mm 47, respectively. The number of arrayed beads was the same among these channels, which indicates that the beads were captured and introduced one by one.

What is claimed is:

1. A device for capturing beads comprising:
a chamber to hold a solution containing a plurality of beads;
a vibration generator to vibrate the chamber;
a long and narrow bead capturing nozzle to capture the beads at a tip thereof;
a suction pump connected to the bead capturing nozzle; and
an actuator to insert the tip of the bead capturing nozzle into the solution in the chamber as well as to lift up the bead capturing nozzle,
wherein an opening at the tip of the bead capturing nozzle is formed as smaller than a diameter of several tens of micrometers to several millimeters of each of the beads, and an outer diameter of the tip of the bead capturing nozzle is larger than the diameter of several tens of micrometers to several millimeters of each of the beads.

2. The device for capturing beads according to claim 1, wherein the vibration generator generates a vibration of a frequency equal to or higher than 20 Hz.

3. The device for capturing beads according to claim 2, wherein the amplitude of the vibration generated by the vibration generator is equal to or larger than 0.1 mm.

4. The device for capturing beads according to claim 1, wherein the vibration generator vibrates the chamber in the direction perpendicular to the axis direction of the bead capturing nozzle.

5. The device for capturing beads according to claim 1, wherein the vibration generator generates vibration such that the center of the chamber is rotated in a plane perpendicular to the axis direction of the bead capturing nozzle.

6. A method for arraying beads comprising the steps of:
inserting, into a solution in a chamber containing a plurality of beads immobilized with a biomolecular probe on the surface thereof, a bead capturing nozzle having an opening smaller than the diameter of the beads formed at the tip thereof and the outer diameter of the tip larger than the diameter of the beads;
exerting a suction force on the tip of the bead capturing nozzle;
vibrating the chamber;
withdrawing the bead capturing nozzle retaining a single bead at the tip via suction from the solution in the chamber; and
introducing the bead retained at the tip of the bead capturing nozzle via suction into a bead array container.

7. The method for arraying beads according to claim 6, wherein a plurality of kinds of beads immobilized with different biomolecular probes are arrayed in a row in the bead array container in orderly sequence.

8. The method for arraying beads according to claim 6, wherein the bead array container is provided with a plurality of flow channels having different inner diameters that are formed on a same chip and beads having different diameters corresponding to each inner diameter are introduced into the plurality of flow channels, respectively.

9. The method for arraying beads according to claim 6, wherein a vibration having a frequency equal to or higher than 20 Hz is provided to the chamber at the step of vibrating the chamber.

10. The method for arraying beads according to claim 6, wherein the amplitude of the vibration is equal to or larger than 0.1 mm.

11. An apparatus for arraying beads comprising:
a stage to retain a plurality of chambers to hold solutions containing a plurality of beads respectively;
a bead capturing nozzle having an opening smaller than the diameter of the beads formed at the tip thereof and an outer diameter of the tip larger than the diameter of the beads;
an actuator to drive the bead capturing nozzle;
a vacuum/pressure unit to develop a negative or positive pressure at the tip of the bead capturing nozzle;
a vibration unit to vibrate the stage;
a holder for bead array container that retains a bead array container to hold beads; and
a control unit, wherein the control unit allows the bead capturing nozzle to be inserted into the vibrating chamber on the stage by controlling the actuator, the bead capturing nozzle to be lifted up from the chamber by controlling the actuator in a state that a single bead is captured at the tip of the bead capturing nozzle by controlling the vacuum/pressure unit to develop a negative pressure at the tip of the bead capturing nozzle, the bead capturing nozzle capturing a single bead at the tip to be moved to the position of the bead array container by controlling the actuator, and the captured bead to be introduced into the bead array container by controlling the vacuum/pressure unit to develop a positive pressure at the tip.

12. The apparatus for arraying beads according to claim 11, wherein a plurality of the bead capturing nozzles are arranged and the holder for bead array container retains the same number of the bead array containers as the number of the bead capturing nozzles.

13. The apparatus for arraying beads according to claim 11, wherein a unit to detect the state that the bead is retained at the tip of the bead retaining nozzle is provided.

14. The apparatus for arraying beads according to claim 11, wherein a unit to detect the state that the bead is introduced into the bead array container is provided.

15. The apparatus for arraying beads according to claim 11, wherein the holder for bead array container retains the bead array container provided with a plurality of flow channels with different inner diameters on a same chip.

16. The device for capturing beads according to claim 1, wherein each of the beads has biomolecular probes or protein immobilized thereon.

17. A device for capturing beads comprising:
a chamber holding a solution containing a plurality of beads each of which has biomolecular probes or protein immobilized thereon;
a vibration generator to vibrate the chamber;
a long and narrow bead capturing nozzle to capture the beads at a tip thereof;
a suction pump connected to the bead capturing nozzle; and
an actuator to insert the tip of the bead capturing nozzle into the solution in the chamber as well as lift up the bead capturing nozzle,
wherein an opening formed at the tip of the bead capturing nozzle is smaller than a diameter of each of the beads, and an outer diameter of the tip of the bead capturing nozzle is larger than the diameter of each of the beads.

18. The device for capturing beads according to claim 17, wherein the beads have diameters of several tens of micrometers to several millimeters.

\* \* \* \* \*